United States Patent
Wang et al.

(10) Patent No.: US 12,351,808 B2
(45) Date of Patent: Jul. 8, 2025

(54) **METHOD FOR PROMOTING EXPRESSION OF FOREIGN GENE IN SOYBEAN, *ARABIDOPSIS* OR TOBACCO USING GENE PROMOTER PRPS28 OR PRPS28-1**

(71) Applicants: Henan University, Zhengzhou (CN); Sanya Institute of Henan University, Sanya (CN)

(72) Inventors: Xuelu Wang, Kaifeng (CN); Haijiao Wang, Kaifeng (CN); Yaqi Peng, Kaifeng (CN)

(73) Assignees: HENAN UNIVERSITY, Zhengzhou (CN); SANYA INSTITUTE OF HENAN UNIVERSITY, Sanya (CN)

( * ) Notice: Subject to any disclaimer, the term of this patent is extended or adjusted under 35 U.S.C. 154(b) by 171 days.

(21) Appl. No.: 18/171,648

(22) Filed: Feb. 20, 2023

(65) Prior Publication Data
US 2023/0340513 A1    Oct. 26, 2023

Related U.S. Application Data

(63) Continuation-in-part of application No. PCT/CN2022/081295, filed on Mar. 17, 2022.

(30) Foreign Application Priority Data

Jul. 2, 2021    (CN) .......................... 202110748338.5

(51) Int. Cl.
C12N 15/82    (2006.01)
C07K 14/415    (2006.01)

(52) U.S. Cl.
CPC ........ *C12N 15/8223* (2013.01); *C07K 14/415* (2013.01); *C12N 15/823* (2013.01)

(58) Field of Classification Search
None
See application file for complete search history.

(56) References Cited

U.S. PATENT DOCUMENTS

2008/0120750 A1    5/2008    Budworth et al.

FOREIGN PATENT DOCUMENTS

| CN | 101044153 A | 9/2007 | |
| CN | 101979563 A | 2/2011 | |
| CN | 102925479 A | 2/2013 | |
| CN | 103667296 A | 3/2014 | |
| CN | 110878304 A | 3/2020 | |
| CN | 113462690 A | * 10/2021 | ........... C07K 14/415 |

OTHER PUBLICATIONS

Gibson et al. (2009) Nature Methods 6(5): 343-345. (Year: 2009).*
Chen et al (2022) aBIOTECH. 3(2):99-109. (Year: 2022).*
Grimwood, J., Glycine max strain Williams 82 clone GM_WBb0065K21, complete sequence, GenBank, Mar. 2009, National Center for Biotechnology Information, United States.
Xianan Liu et al., The Ribosomal Small-Subunit Protein S28 Gene From Helianthus Annuus (Asteraceae) is Down-Regulated in Response to Drought, High Salinity, and Abscisic ACID1, American Journal of Botany, Apr. 2003, pp. 526-531, vol. 90, Botanical Society of America & Brooklyn Botanic Gardens, United States.
Schmutz, J. et al., Glycine max cultivar Williams 82 chromosome 19, Glycine_max_v4.0, whole genome shotgun sequence, Accession No. NC_038255.2, GenBank, Apr. 2021, National Center for Biotechnology Information, United States.
Ning Zhang et al., Isolation and characterization of "GmScream" promoters that regulate highly expressing soybean (*Glycine max* Merr.) genes, Plant Science, 2015, pp. 189-198, vol. 241, Elsevier, Netherlands.
Zhifen Zhang et al., Soybean actin, heat shock protein, and ribosomal protein promoters direct tissue-specific transgene expression in transgenic soybean, In Vitro Cell.Dev.Biol., 2015, pp. 9-18, vol. 51, Springer Science +Business Media, Germany.
Jonni Koia et al., Pineapple translation factor SUI1 and ribosomal protein L36 promoters drive constitutive transgene expression patterns in *Arabidopsis thaliana*, Plant Mol Biol, 2013, pp. 327-336, vol. 81, Springer Science+Business Media, Germany.
Zhiyong Ni et al., Cloning of soybean gma-miR 169c promoter and construction of plant expression vector, Molecular Plant Breeding, 2015, pp. 287-293, vol. 13, No. 2, Hainan Institutes of Biotechnology, China.
Qiong Li et al., Identification and Validation of the Interaction between Patellin 2 and CDKB2;2 in *Arabidopsis thaliana*, Journal of Fudan University, Oct. 2016, pp. 614-622, vol. 55, No. 5, Fudan University, China.

* cited by examiner

*Primary Examiner* — Anne Kubelik
*Assistant Examiner* — Victoria L Deleo
(74) *Attorney, Agent, or Firm* — MATTHIAS SCHOLL P.C.; Matthias Scholl

(57) ABSTRACT

A method for promoting expression of a foreign gene in a plant includes: constructing a recombinant vector including a full-length soybean gene promoter pRPS28 or an intron-including soybean gene promoter pRPS28-I, and introducing the recombinant vector into the plant; the full-length promoter pRPS28 being represented by SEQ ID NO: 2, and the intron-including promoter being represented by pRPS28-I SEQ ID NO: 3.

6 Claims, 20 Drawing Sheets

Specification includes a Sequence Listing.

Bud induction 4 weeks

Shoot elongation

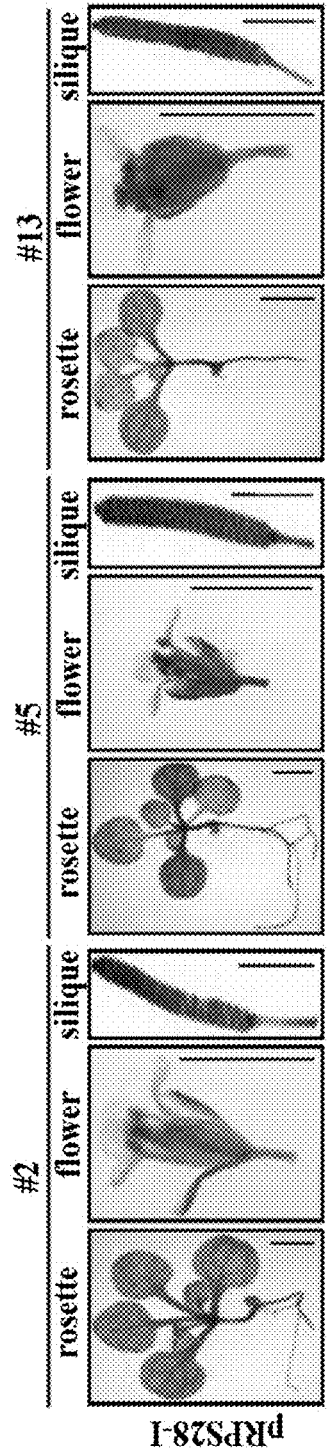
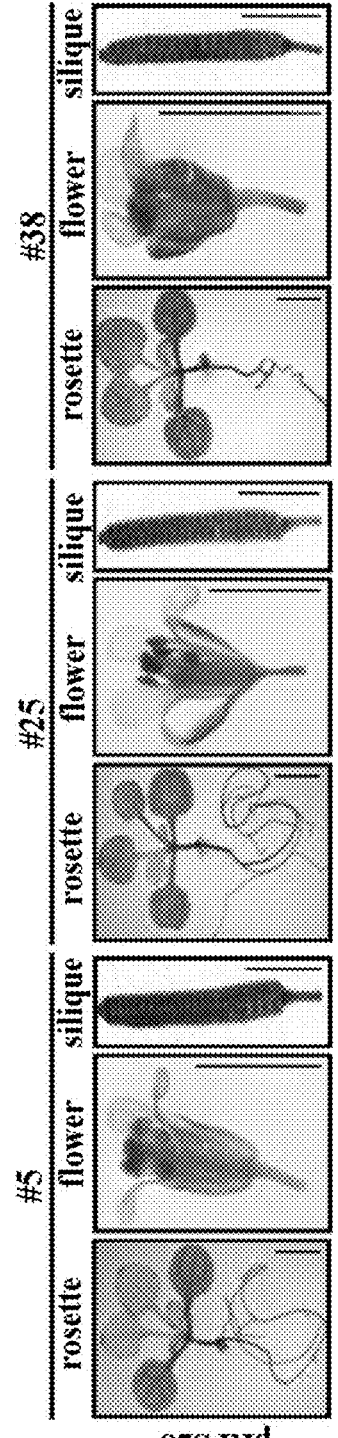
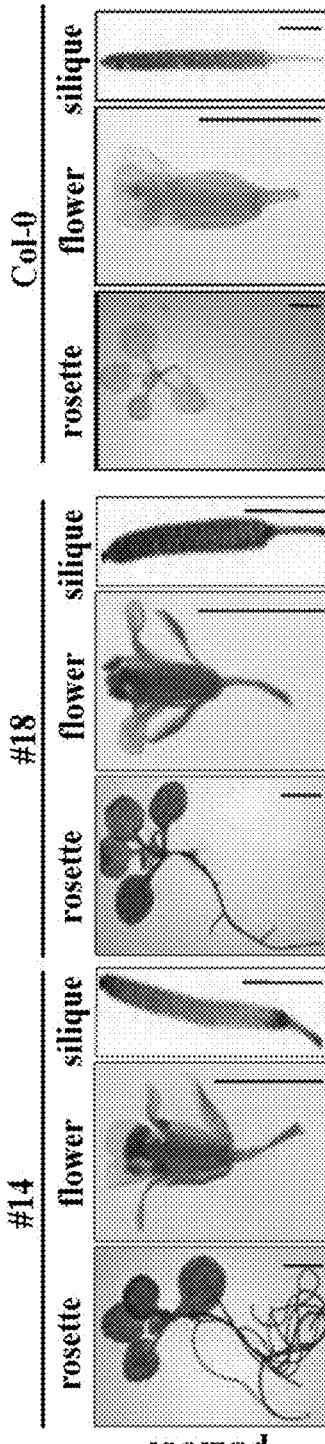
FIG. 8A  FIG. 8B  FIG. 8C  FIG. 8D

METHOD FOR PROMOTING EXPRESSION OF FOREIGN GENE IN SOYBEAN, *ARABIDOPSIS* OR TOBACCO USING GENE PROMOTER PRPS28 OR PRPS28-1

CROSS-REFERENCE TO RELATED APPLICATIONS

This application is a continuation-in-part of International Patent Application No. PCT/CN2022/081295 with an international filing date of Mar. 17, 2022, designating the United States, now pending, and further claims foreign priority benefits to Chinese Patent Application No. 202110748338.5 filed Jul. 2, 2021. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

INCORPORATION-BY-REFERENCE OF SEQUENCE LISTING

This application contains a sequence listing, which has been submitted electronically in XML file and is incorporated herein by reference in its entirety. The XML file, created on Feb. 21, 2023, is named ZZLK-03501-UUS.xml, and is 37,550 bytes in size.

BACKGROUND

The disclosure related to the field of plant genetic engineering, and more particularly, to two soybean promoters pRPS28 and pEIF1-1 and applications thereof in soybean, *Arabidopsis thaliana* and tobacco.

In genetics, a promoter is a sequence of DNA to which proteins bind to initiate the transcription of a single RNA transcript from the DNA downstream of the promoter. The promoter is generally classified into two categories: exogenous promoter and endogenous promoter. An exogenous promoter from viruses, such as the 35S promoter of tobacco mosaic virus, controls the heterologous gene expression, which, however, arises transgenic safety problems. Transgenic silencing is often blamed on the use of the same promoter for expression of different transgenes. The endogenous promoters are more suitable for use in the production of transgenic materials.

Soybean is an important crop that supplies most protein and oil requirements. Soybean establishes symbiotic relationships with rhizobia, which forms nodules in their roots, leading to biological nitrogen fixation. Rhizobia play a fundamental role in nitrogen supply to ecosystems through their ability to fix nitrogen in symbiosis with legumes and promote the growth of plants. Soybean can also be intercropped or rotated with other plants without fertilizer application, thus providing a safe nitrogen source. Soybean has been genetically modified to produce in larger quantities. In addition to the viral promoter, such as the 35S or CMV promoter for soybean transformation, some endogenous promoters, such as the constitutive promoters, inducible promoters, tissue-specific promoters, have also been reported over the years.

Gmubi promoter is a widely used constitutive promoter with high levels of constitutive expression in soybean. The majority of constitutive promoters are chosen during a single soybean developmental stage, and only rarely during the formation of nodules on the soybean roots. When multiple genes are inserted into the genome of a transgenic organism, transgenic silencing occurs.

SUMMARY

The first objective of the disclosure is to provide two soybean reference genes RPS28 and EIF1, as well as two promoters pRPS28 and pEIF1 thereof; the soybean reference genes RPS28 and EIF1 are used as an internal control to determine the expression levels of a target gene in soybean organs at different developmental stages and the development level of root nodules.

The second objective of the disclosure is to provide a use of the promoters pRPS28 and pEIF1 in regulating the constitutive or non-tissue specific expression of soybean genes or other plants (such as tobacco and *Arabidopsis*) genes; specifically, the full length promoter pRPS28 and intron-comprising promoter pRPS28-I, the full length promoter pEIF1 and intron-comprising promoter pEIF1-I are used to promote the overexpression or universal expression of the target genes in soybean, *Arabidopsis*, or tobacco.

To achieve the above objectives, the disclosure provides a method for promoting expression of a foreign gene in a plant, and the method comprises:
  constructing a recombinant vector comprising a full length promoter pRPS28 or an intron-comprising promoter pRPS28-I, a full length promoter pEIF1 or an intron-comprising promoter pEIF1-I as a ubiquitous promoter to promote the expression of a foreign gene in soybean organs;
  the foreign gene is beta-glucuronidase (GUS) gene;
  when introduced into soybean, the promoter promotes the foreign gene to express in cotyledons, radicles, plumules, true leaves, compound leaves, buds, petioles, internodes, roots and root nodules of the soybean;
  when introduced into *Arabidopsis*, the promoter promotes the foreign gene to express in whole plant, flower and pod of the *Arabidopsis*; and
  when introduced into tobacco, the promoter promotes the foreign gene to express in leaves of the tobacco.

Further, the disclosure provides a recombinant vector comprising any one of the promoters.

The recombinant vector is prepared by inserting the one of the promoters into a vector pCAMBIA1391Z-BAR; specifically, inserting the promoters pRPS28, pRPS28-I, pEIF1 and pEIF1-I into the vector pCAMBIA1391Z-BAR to form recombinant vectors pRPS28-GUS-BAR, pRPS28-I-GUS-BAR, pEIF1-GUS-BAR and pEIF1-I-GUS-BAR, respectively. pRPS28-GUS-BAR and pRPS28-I-GUS-BAR have been deposited in China Center for Type Culture Collection (CCTCC) under the Budapest Treaty, respectively with the accession numbers CCTCC M 2025237 and CCTCC M 2025238, and that have been made available to the public.

The disclosure further provides primer sequences for amplification of the genes RPS28 and EIF1.

The gene RPS28 is amplified using the following primers:

```
RPS28-F:
                             (SEQ ID NO: 8)
ATGGAGTCTCAGGTGAAGCAC;

RPS28-R:
                             (SEQ ID NO: 9)
CTAGCGCAATCTTCTTGCTTC.
```

The gene EIF1 is amplified using the following primers:

```
EIF1-F:
                                    (SEQ ID NO: 10)
ATGTCTGAATTAGACGATCAAATTCC;

EIF1-R:
                                    (SEQ ID NO: 11)
TCAGAAACCATGAATCTTGATATGATC.
```

Another objective of the disclosure is to provide primer sequences for amplification of the promoters.

The recombinant vector pRPS28-GUS is amplified using the following primers:
pRPS28-GUS-bar-F:

```
pRPS28-GUS-bar-F:
                                    (SEQ ID NO: 12)
GACCATGATTACGCCAAGCTTCACCACCCAATCCATAACCACCA pRPS28-GUS-bar-R:
                                    (SEQ ID NO: 13)
CCAGTGAATTCCCGGGGATCCCTGATGCAAAACACGAACAAAGAAAG
```

The recombinant vector pRPS28-I-GUS is amplified using the following primers:
pRPS28-I-GUS-bar-F:

```
pRPS28-I-GUS-bar-F:
                                    (SEQ ID NO: 14)
GACCATGATTACGCCAAGCTTCACCACCCAATCCATAACCACCAC pRPS28-I-GUS-bar-R:
                                    (SEQ ID NO: 15)
CCAGTGAATTCCCGGGGATCCCCTGCTCAAACACAATCAACAG
```

The recombinant vector pEIF1-GUS is amplified using the following primers:
pEIF1-GUS-bar-F:

```
pEIF1-GUS-bar-F:
                                    (SEQ ID NO: 16)
GACCATGATTACGCCAAGCTTGGAGAGAAGTTGAACTCTGAGTTGTG pEIF1-GUS-bar-R:
                                    (SEQ ID NO: 24)
CCAGTGAATTCCCGGGGATCCCTGATCGTAAATTTAAGGTTTCG
```

The recombinant vector pEIF1-I-GUS is amplified using the following primers:
pEIF1-I-GUS-bar-F:

```
pEIF-I-GUS-bar-F:
                                    (SEQ ID NO: 16)
GACCATGATTACGCCAAGCTTGGAGAGAAGTTGAACTCTGAGTTGTG pEIF-I-GUS-bar-R:
                                    (SEQ ID NO: 17)
CCAGTGAATTCCCGGGGATCCAAAACTTGACTCACTAAGACCAAGG
```

The promoter pRPS28 has a nucleic acid sequence comprising SEQ ID NO: 2; and the promoter pRPS28-I has a nucleic acid sequence comprising SEQ ID NO: 3.

The promoter pEIF1 has a nucleic acid sequence comprising SEQ ID NO: 5; the promoter pEIF1-I has a nucleic acid sequence comprising SEQ ID NO: 6.

The seventh objective of the disclosure is to provide a method of using the promoter pRPS28 or pRPS28-I to promote the expression of a foreign gene in soybean.

The eighth objective of the disclosure is to provide a method of using the promoter pEIF1 or pEIF1-I to promote the expression of a foreign gene in soybean.

The following advantages are associated with the promoters of the disclosure.

1. The disclosure provides the genes RPS28 and EIF1 that are highly expressed across the soybean tissues at different life cycle stages without being affected by the *Bradyrhizobium japonicum* strain; the different life cycle stages comprise: 8 days after germination of the aerial and underground parts of the soybean, and the various developmental stages of the roots infect with *Bradyrhizobium japonicum* strain (USDA 110).

2. The promoters pRPS28 and pEIF1 drive the constitutive expression of the target gene in different soybean tissues (comprising the root nodules) of the transgenic plants.

3. The promoter pRPS28 promoted the same level of GUS expression as the promoter GmUbi; the promoter pEIF1 comprises an intron sequence that help to maintain the same level of GUS expression as the promoter GmUbi.

BRIEF DESCRIPTION OF THE DRAWINGS

FIGS. 8A-8D show the relative expression of GUS protein under control of the promoters pRPS28, pRPS28-I and pGmUbi in T3 transgenic soybean plants;

DETAILED DESCRIPTION OF THE EMBODIMENTS

The soybean genes RPS28 and EIF1 were amplified; the promoters pRPS28 and pEIF1 were isolated by CTAB method; the promoters pRPS28, pRPS28-I, pEIF1 and pEIF1-I were fused to the GUS gene to form four recombinant vectors pRPS28-GUS, pRPS28-I-GUS, pEIF1-GUS and pEIF1-I-GUS, respectively; the soybean plants were transfected with the vectors; and the GUS protein expression was driven by the promoters pRPS28 and pEIF1. The results showed that the promoters pRPS28, pRPS28-I, pEIF1 and pEIF1-I promoted the expression of the GUS protein in cotyledons, radicles, germs, true leaves, compound leaves, shoots, petioles, internodes, roots and root nodules, which indicated that the promoters pRPS28 and pEIF1 were ubiquitous promoters. The GUS activity was determined in soybean. In addition, the promoters pRPS28 and pEIF1 were used to promote the expression of the GUS protein in *Arabidopsis thaliana* and tobacco.

Example 1

Selection of Genes RPS28 and EIF1

A soybean cultivar Jidou 17 was planted; the true leaves unfolded on 8th day after planting; at the same time, the soybean roots were inoculated with a *Bradyrhizobium japonicum* strain (USDA 110); 1, 2, 4, 6, 8, 10, 15, 20, 25 and 30 days after inoculation, tissues including roots, root nodules, hypocotyls, cotyledons, epicotyls, true leaves, true leaf nodes, compound leaves, internodes, petioles and terminal buds were collected for RNA extraction and sequencing by any conventional method. Specifically, the genes RPS28 and EIF1 are selected through the following steps:

1. finding the ubiquitous genes that were expressed across the soybean tissues at different life cycle stages with RNA-seq; the RNA-seq data for soybean showed the FPKM expression value of each ubiquitous gene; sorting the ubiquitous genes by the FPKM expression values in a decreasing order; and selecting top 20 ubiquitous genes as candidate genes;

2. visualizing the RNA-seq data for the 20 candidate genes; selecting 10 genes that were expressed in the same level across the soybean tissues at different life cycle stages without being affected by the *Bradyrhizobium japonicum* strain (coefficient of variation CV≤0.3); and 3. visualizing the RNA-seq data for the 10 genes; selecting two genes that maintain constant expression levels in all conditions; and analyzing the sequence of the promoter in each gene.

The two genes were named RPS28 and EIF1, respectively; the gene RPS28 encoded a 40S ribosomal protein S2 and has a cDNA sequence comprising SEQ ID NO: 1; the gene EIF1 encoded a eukaryotic initiation factor SUI1 and had a cDNA sequence comprising SEQ ID NO: 4.

The results showed that 1-30 days after the true leaves unfolded, the two genes RPS28 and EIF1 were expressed at high levels in different soybean tissues without being affected by the *Bradyrhizobium japonicum* strain (FIGS. 1A-1C and 2A-2C).

Figure 1A:
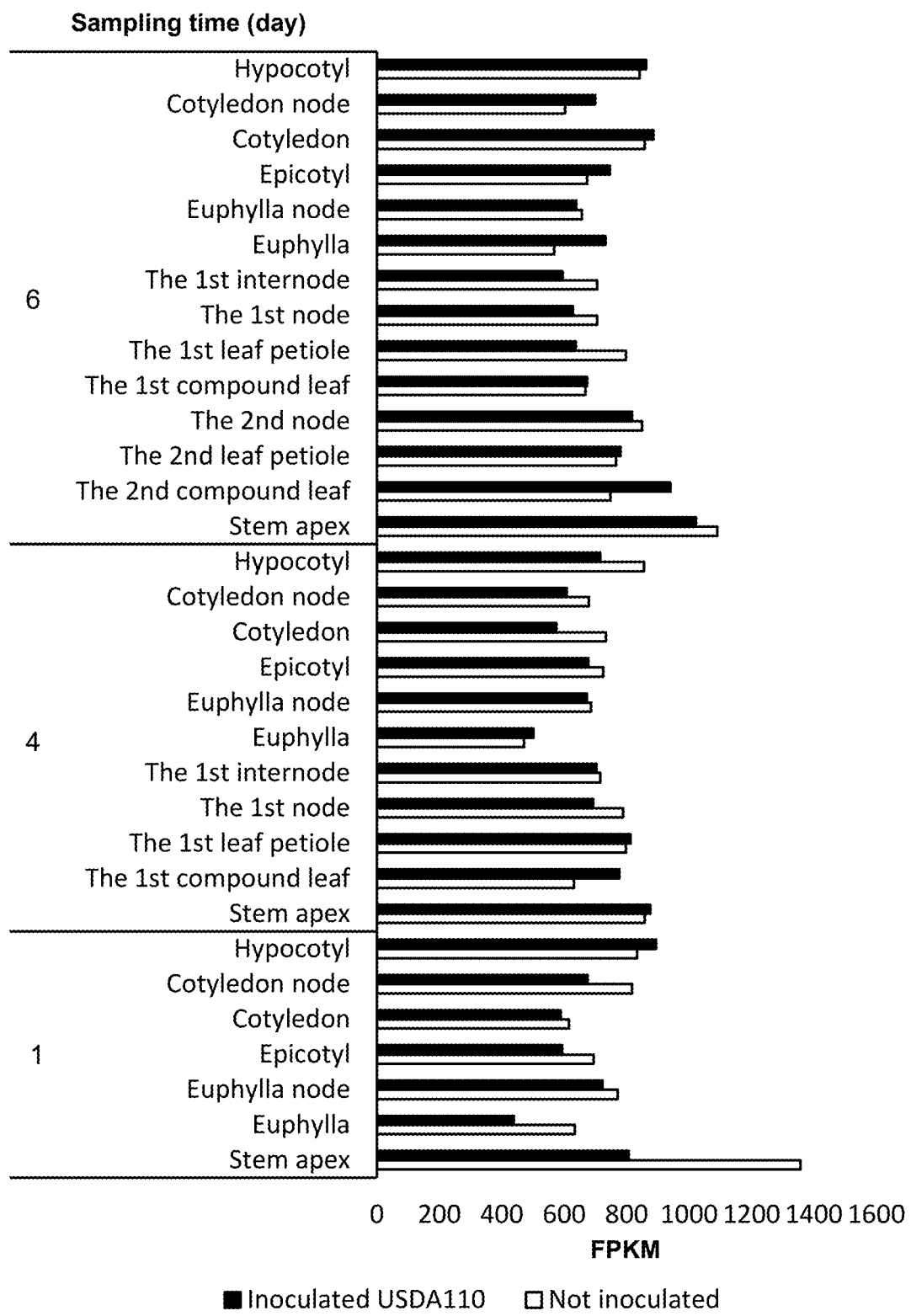
FIGS. 1A-1C are graphs showing the relative expression of the gene RPS28 in soybean tissues at different life cycle stages, as well as in the root nodules.
Figure 1B:
Figure 1C:
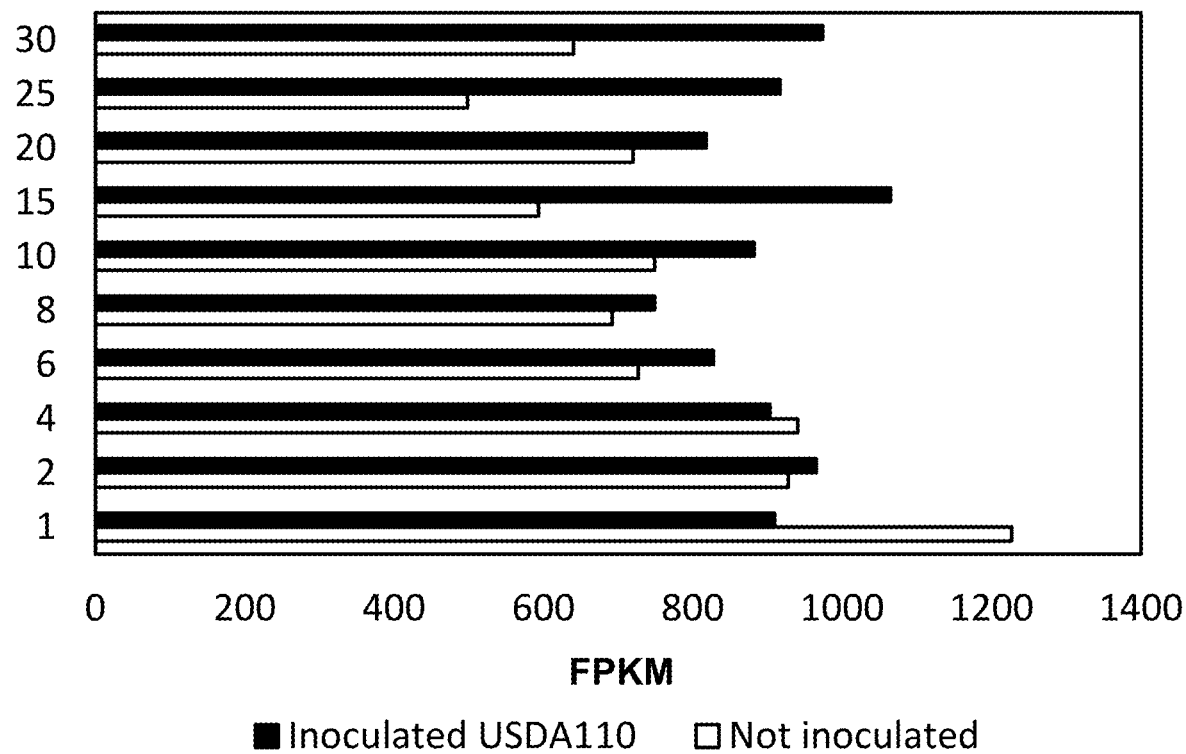

FIGS. 1A-1C were graphs showing the relative expression of the gene RPS28 in the soybean tissues at different life cycle stages, as well as in the root nodules. In FIGS. 1A-1B, when the true leaves unfolded, the soybean roots were inoculated with or without the *Bradyrhizobium japonicum* strain; after 1, 4, 6, 8, 10 and 20 days of inoculation, RNA sequencing was carried out to reveal the presence and quantity of the gene RPS28 in the soybean tissues comprising hypocotyls, cotyledons, epicotyls, true leaves, true leaf nodes, compound leaves, internodes, petioles and terminal buds. The results showed that the gene RPS28 was stably expressed at high levels across the soybean tissues without being affected by the *Bradyrhizobium japonicum* strain. In FIG. 1C, when the true leaves unfolded, the soybean roots were inoculated with or without the *Bradyrhizobium japonicum* strain; after 1, 2, 4, 6, 8, 10, 15, 20, 25, and 30 days of inoculation, RNA sequencing was carried out to reveal the presence and quantity of the gene RPS28 in the roots and the root nodules. The results showed that the gene RPS28 was stably expressed at high levels in the roots and root nodules.

Figure 2A:
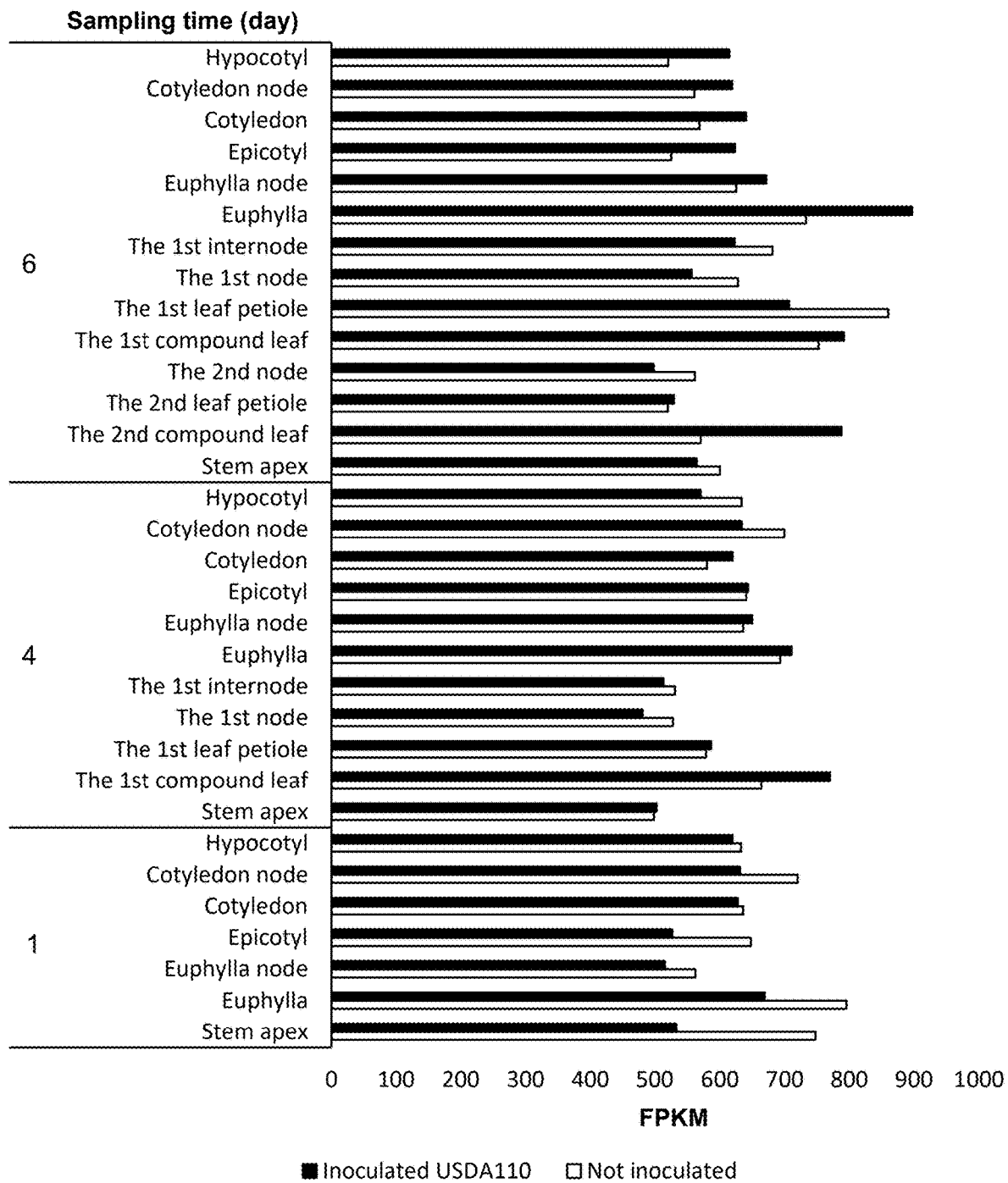
FIGS. 2A-2C are graphs showing the relative expression of the gene EIF1 in soybean tissues at different life cycle stages, as well as in the root nodules.
Figure 2B:
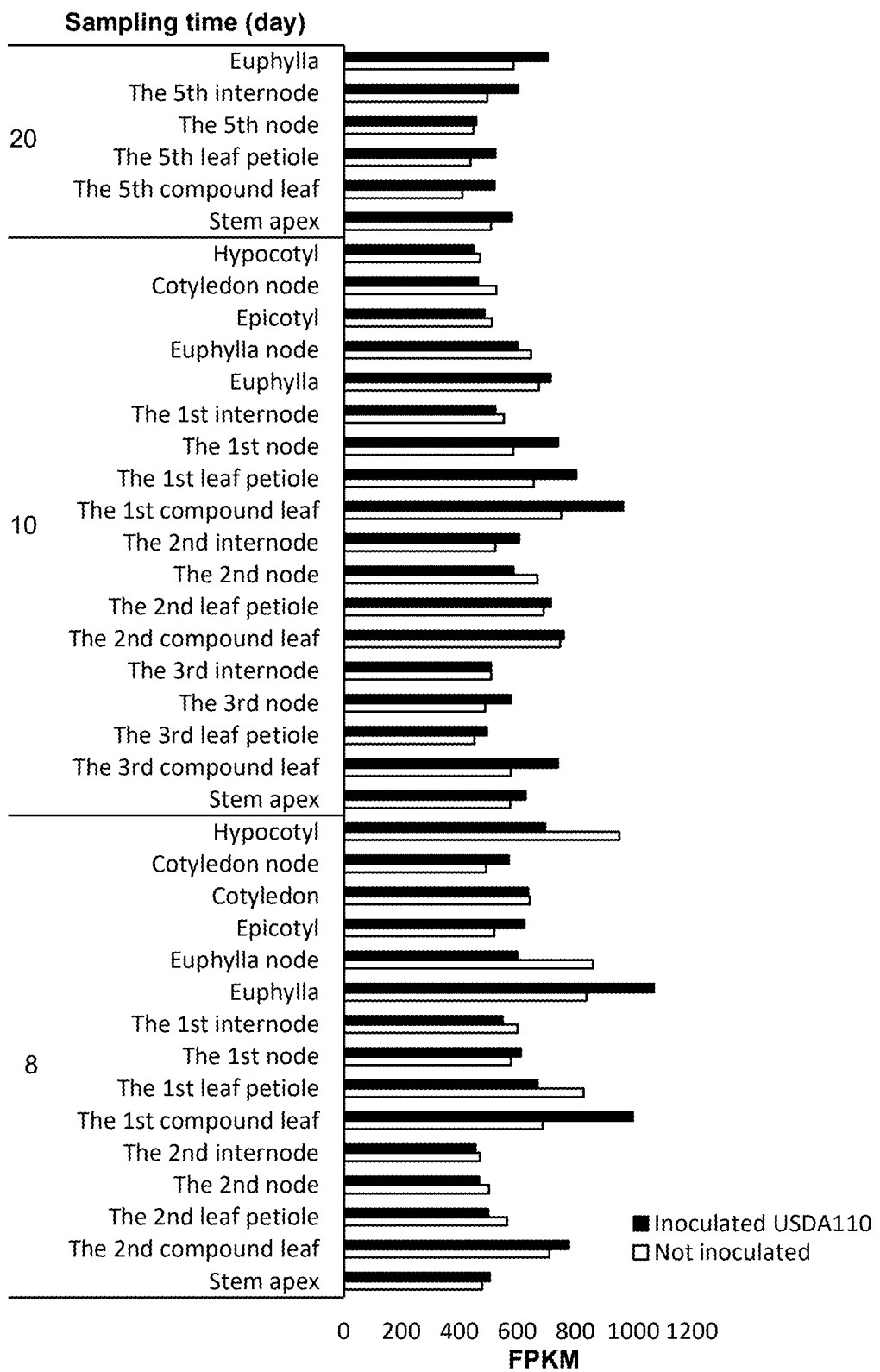
Figure 2C:
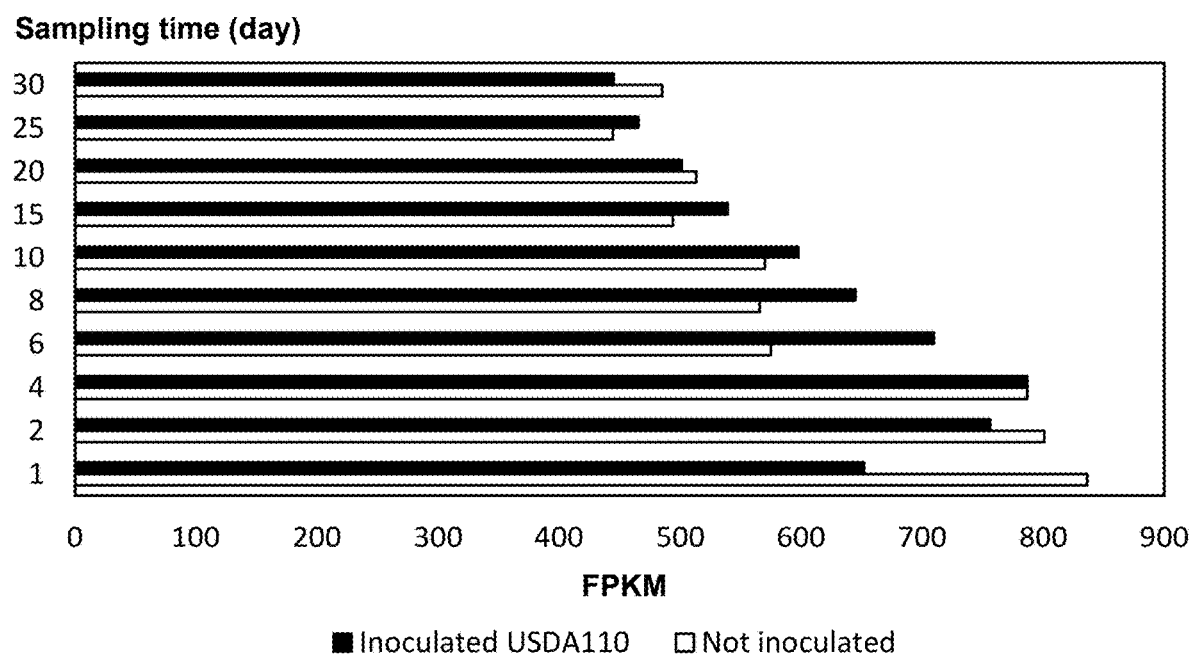

FIGS. 2A-2C were graphs showing the relative expression of the gene EIF1 in soybean tissues at different life cycle stages, as well as in the root nodules.

In FIGS. 2A-2B, when the true leaves unfolded, the soybean roots were inoculated with or without the *Bradyrhizobium japonicum* strain; after 1, 4, 6, 8, 10 and 20 days of inoculation, RNA sequencing was carried out to reveal the presence and quantity of the gene EIF1 in the soybean tissues comprising hypocotyls, cotyledons, epicotyls, true leaves, true leaf nodes, compound leaves, internodes, petioles and terminal buds. The results showed that the gene EIF1 was stably expressed at high levels across the soybean tissues without being affected by the *Bradyrhizobium japonicum* strain. In FIG. 2C, when the true leaves unfolded, the soybean roots were inoculated with or without the *Bradyrhizobium japonicum* strain; after 1, 2, 4, 6, 8, 10, 15, 20, 25, and 30 days of inoculation, RNA sequencing was carried out to reveal the presence and quantity of the gene EIF1 in the roots and the root nodules. The results showed that the gene EIF1 was stably expressed at high levels in the roots and root nodules.

Example 2

Amplification of Promoters pRPS28 and pEIF1

According to the results in Example 1, the genes RPS28 and EIF1 had a genome sequence spanning of 2357 bp and 1640 bp, respectively; and each gene contained an intron sequence between ATG start codon and 5'UTR. Therefore, a full-length promoter and an intron-comprising promoter were designed for each gene and named pRPS28, pRPS28-I, pEIF1 and pEIF1-I.

Genomic DNA was extracted from the soybean cultivar Williams 82 (WS82) by CTAB method, used as a template DNA for amplification of the DNA fragments RPS28, RPS28-1, pEIF1 and pEIF1-I. PCR amplification was performed as follows:

A 50 μL reaction contained 1 μL (about 100 ng) of the template DNA, 25 μL 2×Phanta Max Super-Fidelity buffer, 1 μL of 10 mM dNTP, 5 μL of 4 μM primer (i.e. 2 μL of each primer with a concentration of 10 mM), and 1 μL of phanta MAX Super-Fidelity DNA enzyme, and 17 μL of ddH2O (sterile deionized water).

The PCR cycling and running parameters were described as follows: denaturation at 94° C. for 2 min; 30 cycles of 94° C. for 10 s, 58° C. for 30 s, and 72° C. for 30 s; and the final extension at 72° C. for 5 min.

The gene RPS28 was amplified using the following primers:

```
F:
                                          (SEQ ID NO: 8)
   ATGGAGTCTCAGGTGAAGCAC;

R:
                                          (SEQ ID NO: 9)
   CTAGCGCAATCTTCTTGCTTC.
```

The gene EIF1 was amplified using the following primers:

```
F:
                                          (SEQ ID NO: 10)
   ATGTCTGAATTAGACGATCAAATTCC

R:
                                          (SEQ ID NO: 11)
   TCAGAAACCATGAATCTTGATATGATC
```

The promoter pRPS28 was amplified using the following primers:

```
pRPS28-F:
                                             (SEQ ID NO: 25)
CACCACCCAATCCATAACCACCAC pRPS28-R:
                                             (SEQ ID NO: 26)
CTGATGCAAAACACGAACAAAGAAAG
```

The promoter pRPS28 has a nucleic acid sequence comprising SEQ ID NO: 2;

The promoter pRPS28-I was amplified using the following primers:

```
pRPS28-I-F:
                                             (SEQ ID NO: 25)
CACCACCCAATCCATAACCACCAC pRPS28-I-R:
                                             (SEQ ID NO: 27)
CCTGCTCAAACACAATCAACAG
```

The promoter pRPS28-I has a nucleic acid sequence comprising SEQ ID NO: 3.

The gene pEIF1 was amplified using the following primers:

```
pEIF1-F:
                                             (SEQ ID NO: 28)
GGAGAGAAGTTGAACTCTGAGTTGTG pEIF1-R:
                                             (SEQ ID NO: 29)
CTGATCGTAAATTTAAGGTTTCG
```

The promoter pEIF1 has a nucleic acid sequence comprising SEQ ID NO: 5.

The promoter pEIF1-I was amplified using the following primers:

```
pEIF1-I-F:
                                             (SEQ ID NO: 28)
GGAGAGAAGTTGAACTCTGAGTTGTG pEIF1-I-R:
                                             (SEQ ID NO: 30)
AAAACTTGACTCACTAAGACCAAAGG
```

The promoter pEIF1-I has a nucleic acid sequence comprising SEQ ID NO: 6.

Example 3

Transformation of Promoters pRPS28 and pEIF1 into Soybean

Figure 3:
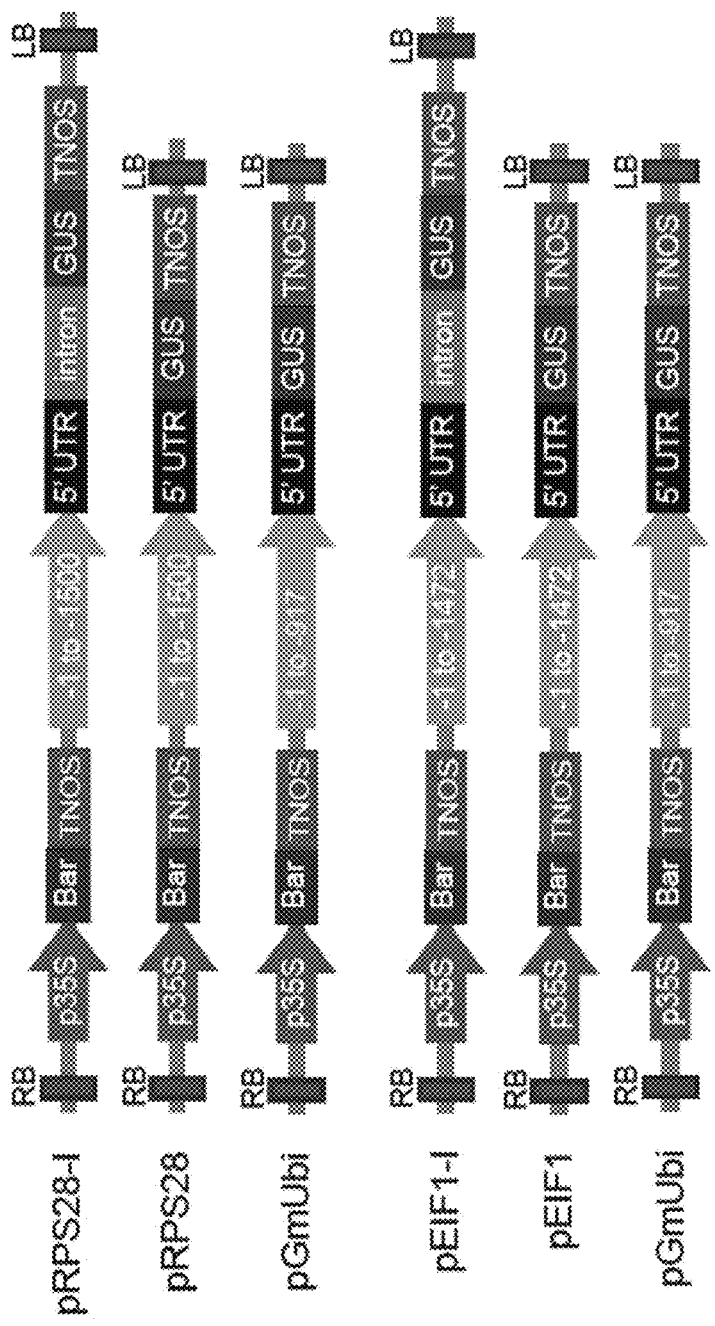
FIG. 3 shows two maps of two recombinant vectors comprising a promoter pRPS28 and a promoter pEIF1, respectively.
Figure 4A:
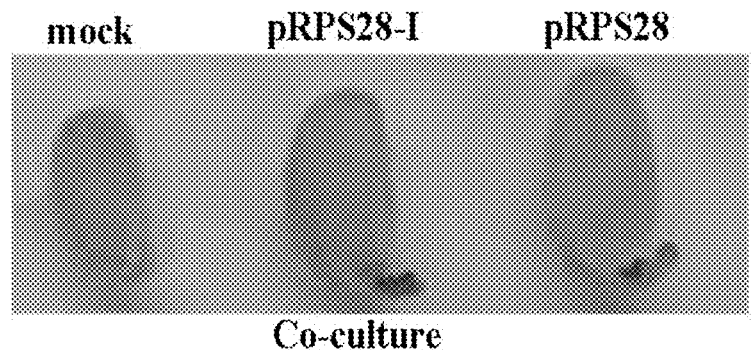
FIGS. 4A-4E show the GUS activity controlled by the promoters pRPS28 and pEIF1 during genetic transformation.
Figure 4B:
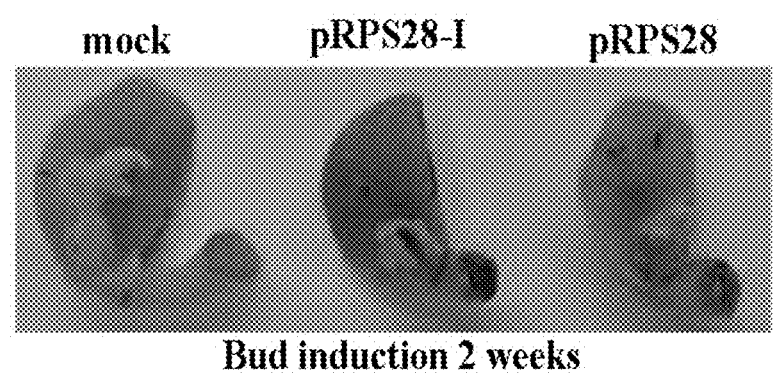
Figure 4C:
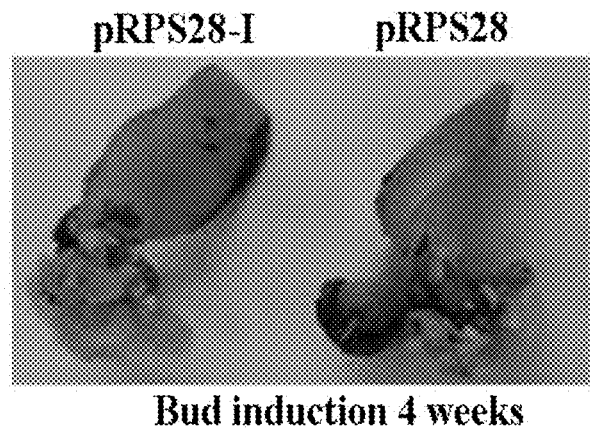
Figure 4D:
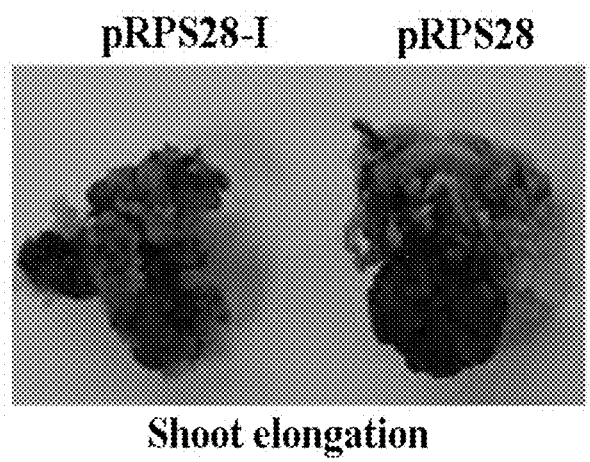
Figure 4E:
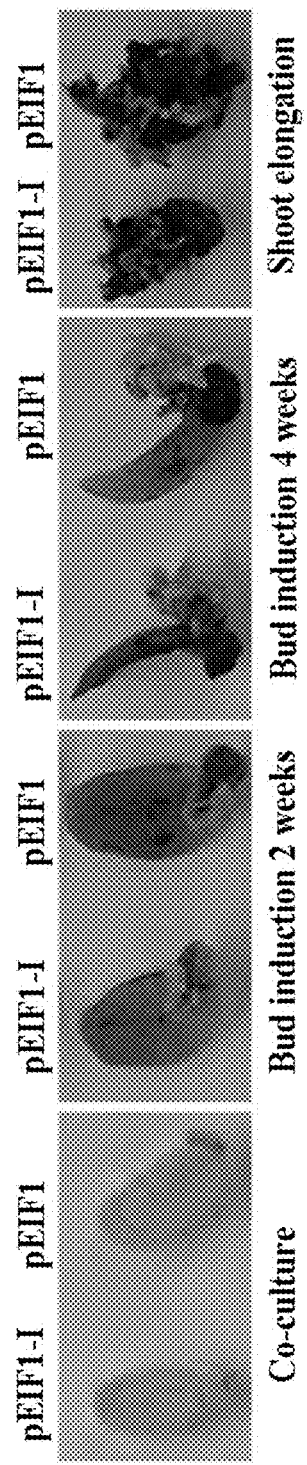

The GUS protein under control of the promoters pRPS28 and pEIF1 was stably expressed during the transformation process, such as co-cultivation, shoot induction and shoot elongation. As shown in FIG. 3, the recombinant vectors pRPS28-GUS, pRPS28-I-GUS, pEIF1-GUS and pEIF1-I-GUSI-GUS were prepared; and a recombinant vector pGmUbi-GUS was constructed as a control.

1. Construction of a Recombinant Vector

In Example 2, the DNA fragments pRPS28, pRPS28-I, pEIF1 and pEIF1-I were used as templates and inserted into a vector pCAMBIA1391Z-BAR by seamless cloning method, and the recombinant vectors pRPS28-GUS-BAR, pRPS28-I-GUS-BAR, pEIF1-GUS-BAR and pEIF1-I-GUS-BAR were prepared; the recombinant vector pGmUbi-GUS-BAR was constructed as a control; the five recombinant vectors were transformed into the soybean cultivar WS82.

PCR amplification was performed as follows:

A 50 μL reaction contained 1 μL (about 100 ng) of the template DNA, 25 μL 2×Phanta Max Super-Fidelity buffer, 1 μL of 10 mM dNTP, 5 μL of 4 μM primer (i.e. 2 μL of each primer with a concentration of 10 mM), and 1 μL of phanta MAX Super-Fidelity DNA enzyme, and 17 μL of ddH2O (sterile deionized water).

The PCR cycling and running parameters were described as follows: denaturation at 94° C. for 2 min; 30 cycles of 94° C. for 10 s, 58° C. for 30 s, and 72° C. for 30 s; and the final extension at 72° C. for 5 min.

The recombinant vector pRPS28-GUS was amplified using the following primers:

pRPS28-GUS-bar-F:

```
pRPS28-GUS-bar-F:
                                             (SEQ ID NO: 14)
GACCATGATTACGCCAAGCTTCACCACCCAATCCATAACCACCAC pRPS28-GUS-bar-R:
                                             (SEQ ID NO: 13)
CCAGTGAATTCCCGGGGATCCCTGATGCAAAACACGAACAAAGAAAG
```

The recombinant vector pRPS28-I-GUS was amplified using the following primers:

pRPS28-I-GUS-bar-F:

```
pRPS28-I-GUS-bar-F:
                                             (SEQ ID NO: 14)
GACCATGATTACGCCAAGCTTCACCACCCAATCCATAACCACCAC pRPS28-I-GUS-bar-R:
                                             (SEQ ID NO: 15)
CCAGTGAATTCCCGGGGATCC CCTGCTCAAACACAATCAACAG
```

The recombinant vector pEIF1-GUS was amplified using the following primers:

pEIF1-GUS-bar-F:

```
pEIF1-GUS-bar-R:
                                             (SEQ ID NO: 16)
GACCATGATTACGCCAAGCTT GGAGAGAAGTTGAACTCTGAGTTGTG pEIF1-GUS-bar-R:
                                             (SEQ ID NO: 24)
CCAGTGAATTCCCGGGGATCC CTGATCGTAAATTTAAGGTTTCG
```

The recombinant vector pEIF1-I-GUS was amplified using the following primers:

pEIF1-I-GUS-bar-F:

```
pEIF-I-GUS-bar-F:
                                             (SEQ ID NO: 16)
GACCATGATTACGCCAAGCTT GGAGAGAAGTTGAACTCTGAGTTGTG pEIF-I-GUS-bar-R:
                                             (SEQ ID NO: 17)
CCAGTGAATTCCCGGGGATCC AAAACTTGACTCACTAAGACCAAAGG
```

The recombinant vector pGmUbi-GUS was amplified using the following primers:
pGmUbi-GUS-bar-F:

```
pGmUbi-GUS-bar-F:
                                      (SEQ ID NO: 18)
GACCATGATTACGCCAAGCTT GGGCCCAATATAACAACGAC pGmUbi-GUS-bar-R:
                                      (SEQ ID NO: 17)
CCAGTGAATTCCCGGGGATCCAAAACTTGACTCACTAAGACCAAAGG (SEQ ID NO: 19)
CCAGTGAATTCCCGGGGATCC ctgtcgagtcaacaatcaca
```

The vector pCAMBIA1391Z-BAR was prepared by linearizing the vector pCAMBIA1391Z with the restriction enzyme XhoI, replacing the gene HygR with the gene BAR by the seamless cloning method in the presence of the following primers:

```
pCAMBIA1391Z-BAR-F:
                                      (SEQ ID NO: 20)
TACAAATCTATCTCTCTCGAGatgagcccagaacgacgcccg;

pCAMBIA1391Z-BAR-R:
                                      (SEQ ID NO: 21)
CATTATTATGGAGAAACTCGAGTCAGATCTCGGTGACGGGCAGGAC
```

The seamless cloning method was performed by conventional techniques and accordingly was not described in detail herein.

2. Soybean Genetic Transformation and GUS Histochemical Staining

The recombinant vectors were transformed into the soybean cultivar WS82 by transformation of the cotyledon nodes with *Agrobacterium tumefaciens* EHA105 (Luth D, Warnberg K, Wang K. Soybean [*Glycine max* (L.) Merr]. Methods Mol Biol. 2015; 1223:275-84. doi: 10.1007/978-1-4939-1695-5_22. PMID: 25300848.)

The transformation process was modified as follows:

Sterilization and germination of soybean seeds: the healthy seeds were separated from damaged and diseased soybean seeds, sterilized with chlorine gas (that was generated by slowly adding 5 mL of concentrated hydrochloric acid to 100 mL of sodium hypochlorite along the wall of a 250 ml beaker, followed by sterilization for 16 hours). The sterilized seeds were transferred in a culture medium and placed in an incubator at 22° C. for 16-24 hours in the dark.

Activation of *Agrobacterium* and preparation of an infiltration solution: the five recombinant vectors were transformed into the *Agrobacterium tumefaciens* EHA105 by electroshock method; and the *Agrobacterium tumefaciens* EHA105 grown on an LB agar plate with kanamycin. Positive clones were inoculated into an LB liquid culture medium comprising kanamycin and incubated in a shaker overnight at 220 rpm and 28° C. 250 μL of the bacterial solution was spread on the surface of the LB agar and incubated overnight at 28° C. The bacterial sample was picked up by an inoculation loop, resuspended in the liquid culture medium, and grown to an optical density at 600 nM (OD600) of 0.5-0.6 that was measured by a spectrophotometer.

Preparation and infection of an explant: after seed germination, the hypocotyl with a length of 3-5 mm was collected, and two cotyledons was separated, followed by removal of the seed coat and the primary bud; the cotyledonary nodes were cut through to form an explant. The explant was subsequently immersed in an infiltration solution and oscillated on a horizontal rotator (at a rotation speed of 50-80 r/min) for 30 min.

Co-cultivation: the explant was transferred from the infiltration solution onto a solid co-culture plate covered with a layer of sterile filter paper, with 15-20 explants in each plate; the explants were then cultivated in the incubator at 22° C. for 3-5 days in the dark; and stained with GUS.

Screening and culture for regeneration (Luth D, Warnberg K, Wang K. Soybean [*Glycine max* (L.) Merr]. Methods Mol Biol. 2015; 1223:275-84. doi: 10.1007/978-1-4939-1695-5_22. PMID: 25300848.): shoot induction: after co-cultivation for 3-5 days, the explants were transferred in a culture medium, with 5 explants in each plate; the culture was maintained at 25° C. with 16 hours of light and 8 hours of darkness; the repetitive subculture was carried out every two weeks for a total of two times. GUS staining was performed on the bud explants. Shoot elongation: the dead shoots and cotyledons were removed from the explants; the explants were transferred in a culture medium, with 5 explants in each plate; the culture was maintained at 25° C. with 16 hours of light and 8 hours of darkness; and repetitive subculture was carried out every three weeks for a total of 2-4 times. GUS staining was performed on the explants. Root induction: when the seedlings grown to a length of 3 cm, the roots were collected and grown on a culture medium; the culture was maintained at 25° C. with 16 hour of light and 8 hour of darkness.

FIGS. 4A-4E showed the relative expression of the GUS protein under control of the promoters pRPS28 and pEIF1; where (a) cultivation; (b) shoot induction after 2 weeks; (c) shoot induction after 4 weeks; and (d) shoot elongation; in FIGS. 4A-4E, the results showed that the promoter pRPS28 and pEIF1 promoted the expression of the GUS protein during the transformation process. Seedling refining and transplanting: when the roots regenerated and at least two compound leaves emerged, the cultured medium was removed from the roots; the regenerated plant was planted in a flowerpot comprising sterilized vermiculite and grown in the incubator (at 25° C. with a relative humidity of 85% and a light intensity 90 μM/m2/s, as well as 16 hours of light and 8 hours of darkness) for 5-7 days. The seedlings became robust, were transplanted into a large flowerpot (comprising nutrient soil and vermiculite mixed in a ratio of 1:1), and moved to a growth room (at 28±2° C. with a relative humidity of 40%-60%, a light intensity 90 μM/m2/s, as well as 13.5 hours of light and 10.5 hours of darkness) until they reached maturity.

Identification of the regenerated plant by use of the T1 soybean plants: the genomic DNA was extracted from the leaves of the T1 transgenic soybean plant and used as a template for amplification of the BAR gene in the T1 soybean plants; and the specific band was amplified from only the transgenic soybean plants.

PCR amplification was performed as follows: a 10 μL PCR reaction contained 0.5-1 μL of template DNA, 5 μL of 2×Taq Mix, 0.5 μL of primers (i.e. 0.25 μL of BAR-F and 0.25 μL of BAR-R), and ddH2O (deionized water) added to reach a total volume of 10 μL.

The PCR cycling and running parameters were described as follows: denaturation at 94° C. for 2 min; 30 cycles of 94° C. for 10 s, 58° C. for 30 s, and 72° C. for 30 s; and the final extension at 72° C. for 5 min.

The gene BAR was amplified using the following primers:

```
BAR-F:
                                          (SEQ ID NO: 22)
ATGAGCCCAGAACGACGCCCGGCC

BAR-R:
                                          (SEQ ID NO: 23)
TTAGATCTCGGTGACGGGCAGGAC
```

The BAR gene comprised a nucleic acid sequence comprising SEQ ID NO: 7.

3. GUS Histochemical Assay

Tissues of the homozygous transgenic plants were collected at 5 and 15 days after cultivation and subjected to GUS histochemical assay. Specifically, the plant tissues were fixed with acetone for 30-60 min, washed with a GUS-staining buffer, infiltrated with a GUS-staining solution (comprising GUS buffer and 1 mg/L X-GLuc), placed under vacuum for 30-60 min in darkness, and incubated for 4 h at 37° C. in darkness, dehydrated with ethanol, and examined under a dissecting microscope.

Figure 5A:
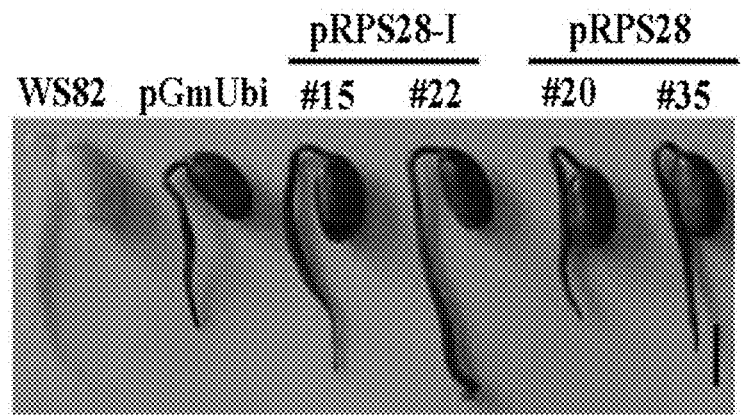
FIGS. 5A-5G show the relative expression of GUS protein under control of the promoter pRPS28 in T2 transgenic soybean plants.
Figure 5B:
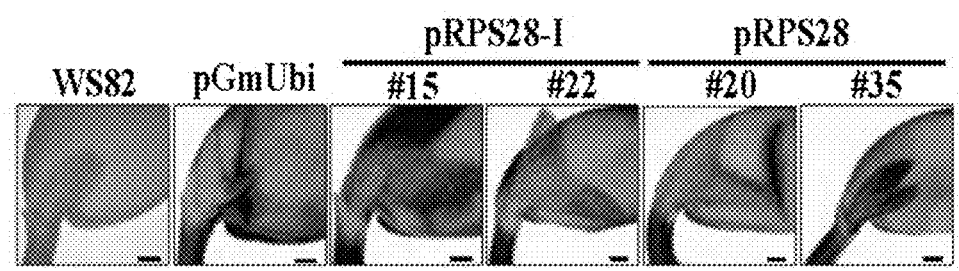
Figure 5C:
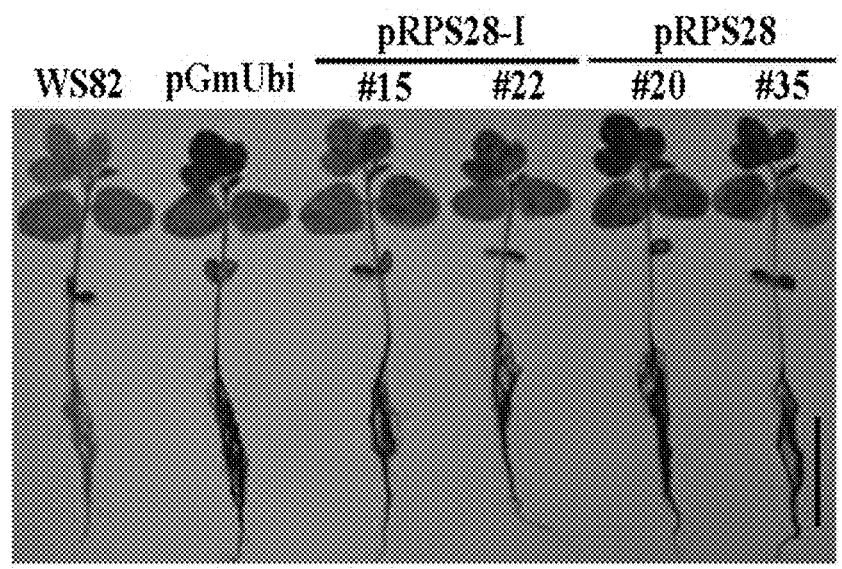
Figure 5D:
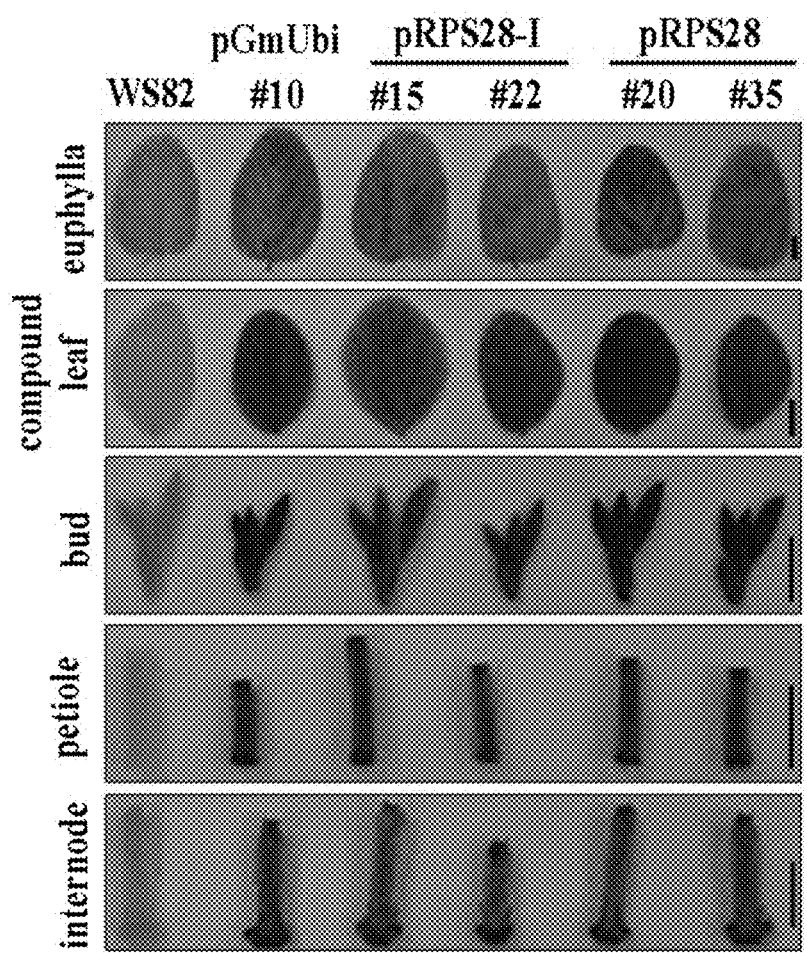
Figure 5E:
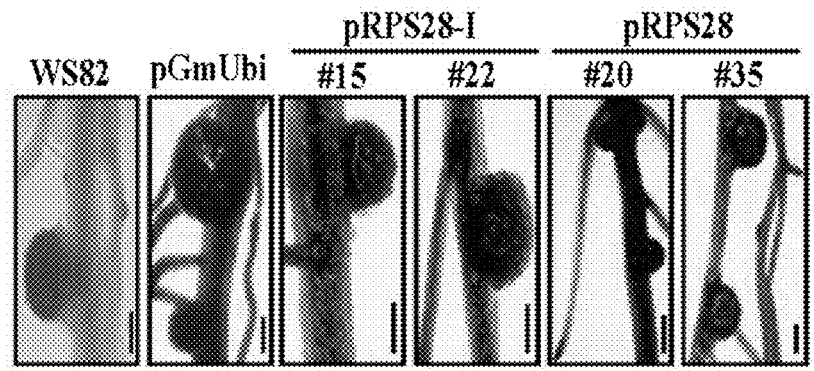
Figure 5F:
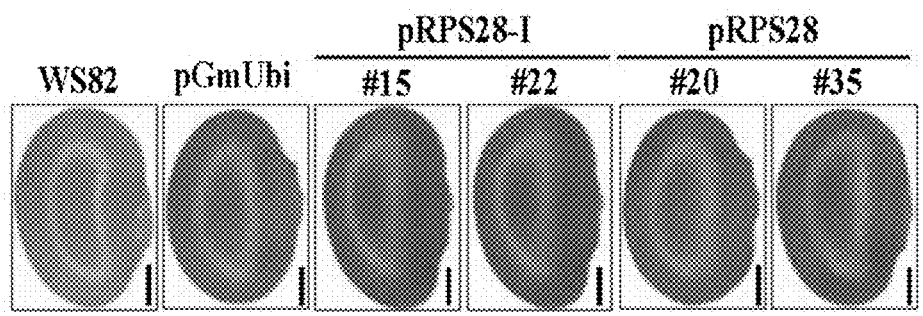
Figure 5G:
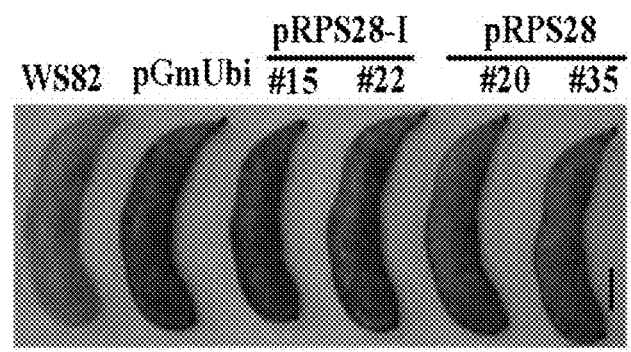

FIGS. 5A-5G showed the relative expression of GUS protein under control of the promoter pRPS28 in different tissues of a T2 transgenic soybean plant. FIG. 5A showed the soybean germinated for 5 days; FIG. 5B showed the embryo; FIG. 5C showed the soybean grown for 15 days; FIG. 5D showed the true leaf, compound leaf, bud, petiole, and internode of the soybean grown for 15 days; FIG. 5E showed the root and root nodule; FIG. 5F showed the immature embryo; and FIG. 5G showed the pod.

Figure 6A:
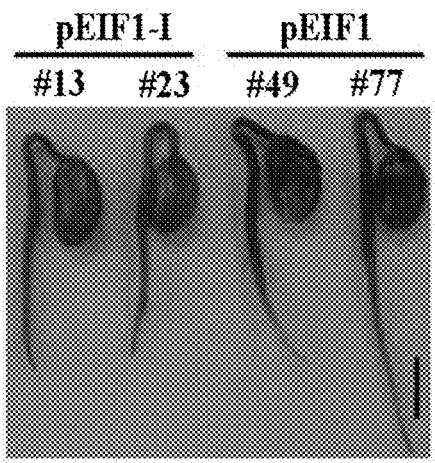
FIGS. 6A-6G show the relative expression of GUS protein under control of the promoter pEIF1 in T2 transgenic soybean plants.
Figure 6B:
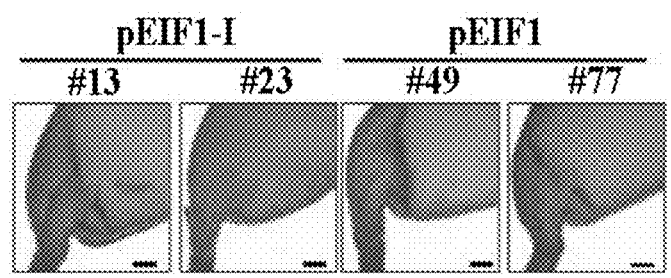
Figure 6C:
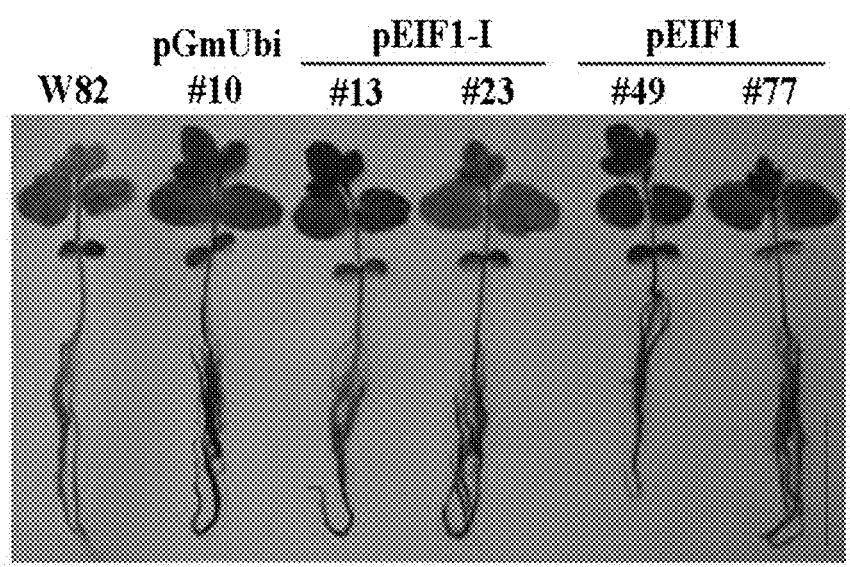
Figure 6D:
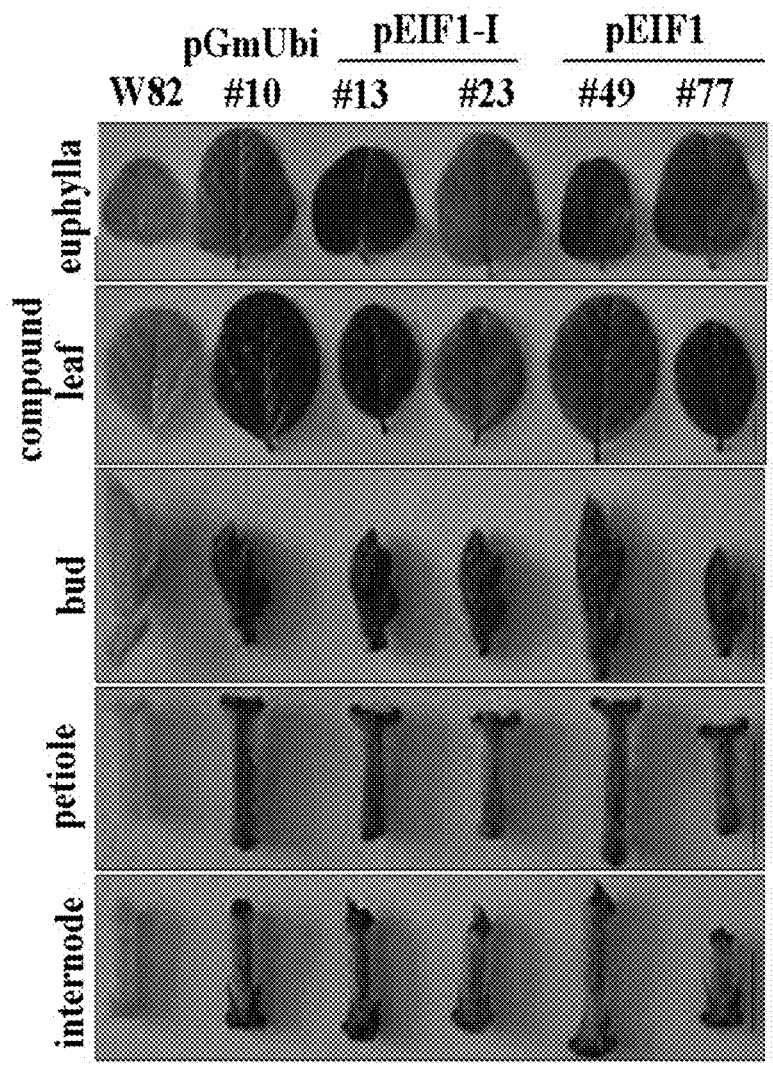
Figure 6E:
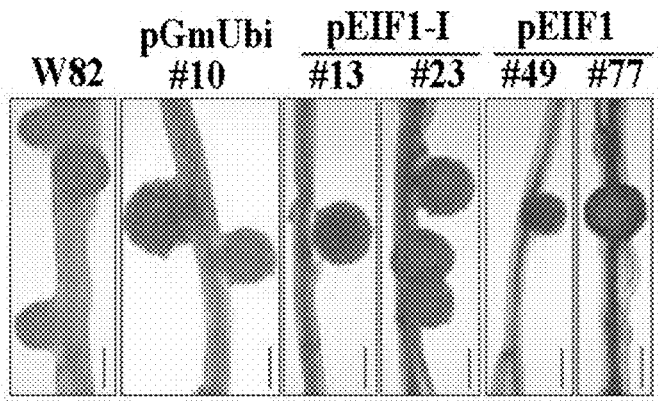
Figure 6F:
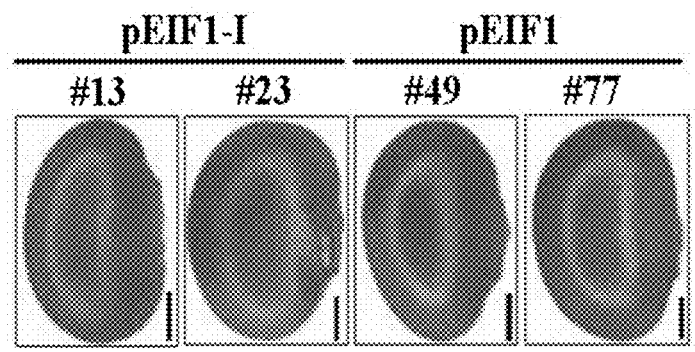
Figure 6G:
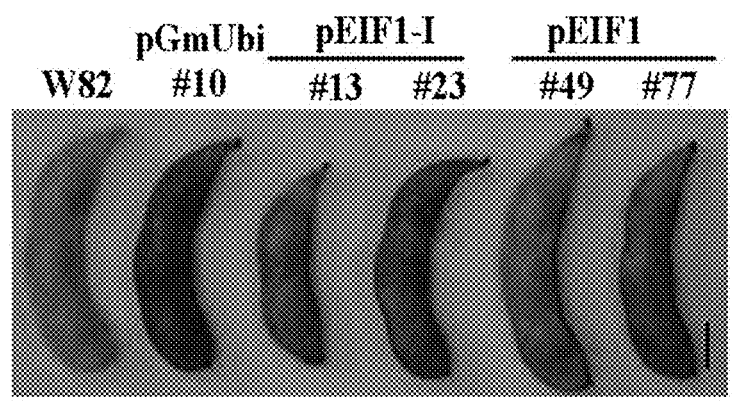

FIGS. 6A-6G showed the relative expression of GUS protein under control of the promoter pEIF1 in different tissues of a T2 transgenic soybean plant; FIG. 6A showed the soybean germinated for 5 days; FIG. 6B showed the embryo; FIG. 6C showed the soybean grown for 15 days; FIG. 6D showed the true leaf, compound leaf, bud, petiole, and internode of the plant grown for 15 days; FIG. 6E showed the root and root nodule; FIG. 6F showed the immature embryo; and FIG. 6G showed the pod.

5 days after germination, the GUS protein under the control of the promoters pRPS28, pRPS28-I, pEIF1 and pEIF1-I were expressed in the cotyledon, radicle, embryo of the transgenic soybean plant; 15 days after germination, the GUS protein under the control of the promoters pRPS28, pRPS28-I, pEIF1 and pEIF1-I were expressed in the true leaf, compound leaf, shoot, petiole, internode, root and root nodule, and even expressed in the immature embryo, pod and seed in the transgenic soybean plant; and the results showed that the promoters pRPS28 and pEIF1 are ubiquitous promoters.

4. Comparison of GUS Activities Controlled by Promoters pRPS28, pEIF1 and pGmUbi in Soybean.

The T3 homozygous transgenic plants comprising the recombinant vectors pRPS28-GUS-BAR, pRPS28-I-GUS-BAR, pEIF1-GUS-BAR, pEIF1-I-GUS-BAR and pGmUbi-GUS-BAR were cultivated for 15 days; the tissues such as root, trifoliate leaf, true leaf, and cotyledon were collected and stored in liquid nitrogen. GUS activity was quantified using 4-Methylumbelliferone (4-MU) as a fluorometric standard and 4-MUG as a fluorometric substrate; the fluorescent compound was detected using a fluorimeter with an excitation wavelength of 455 nm; a standard curve of 4-MU fluorescence was generated and used to quantify the GUS activity (pmol MU/min/mg)

Figure 7:
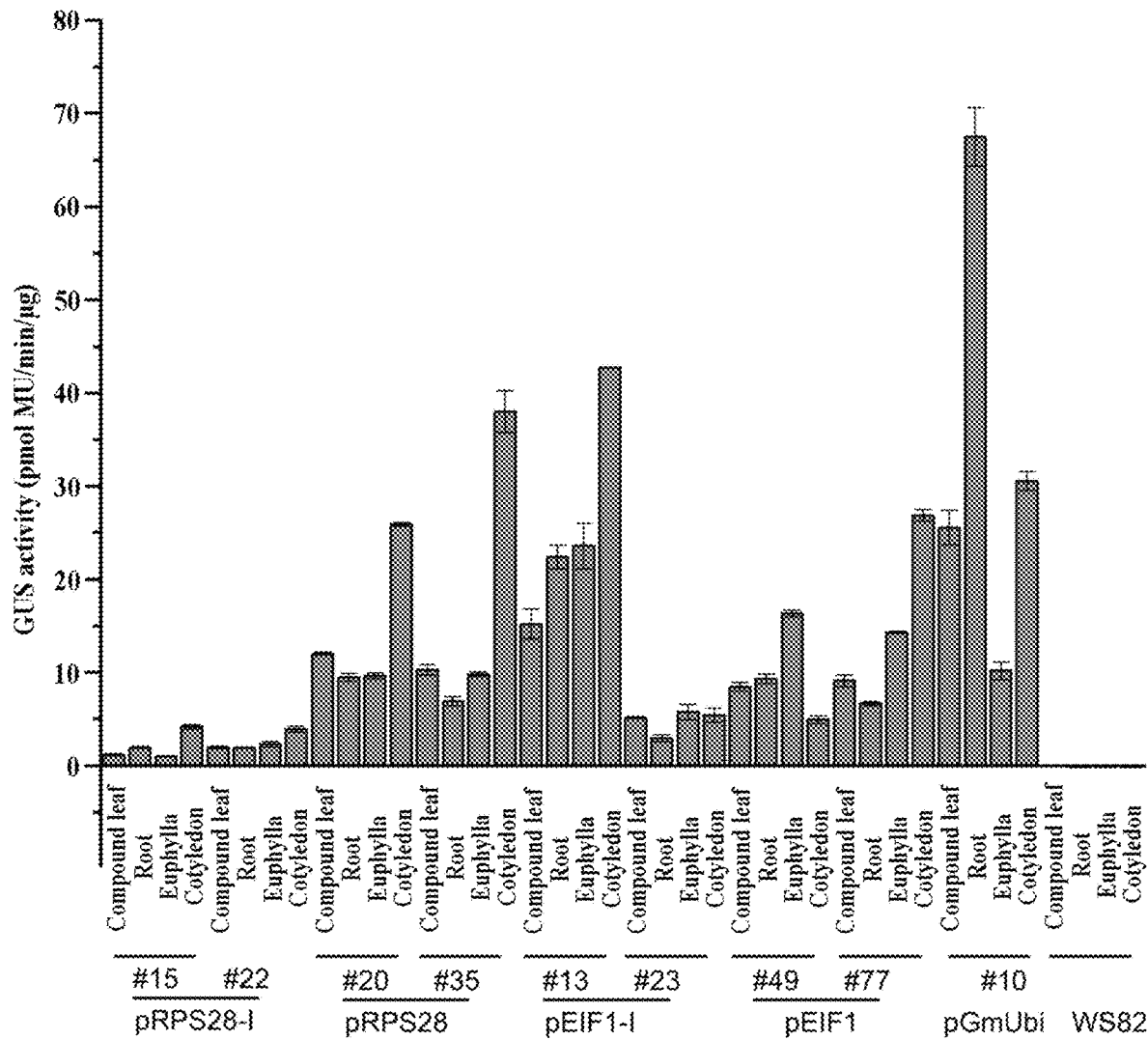
FIG. 7 is a graph showing the GUS activity controlled by the promoters pRPS28, pRPS28-I, pEIF1, pEIF1-I and pGmUbi in transgenic soybean plants.

FIG. 7 showed the GUS activity controlled by the promoters pRPS28, pRPS28-I, pEIF1, pEIF1-I and pGmUbi in the soybean tissues such as root, compound leaf, true leaf, cotyledon. From the results, the promoters pRPS28, pRPS28-I, pEIF1 and pEIF1-I promoted the ubiquitous expression of the GUS protein across the soybean tissues; the promoter pRPS28 promoted higher levels of GUS expression than the promoter pRPS28-I; and the promoter pEIF1-I promoted higher levels of GUS expression than the promoter pEIF1. The GUS activity in the cotyledon of a soybean line #20 that was controlled by the promoter pRPS28 was 25.93 pmolMU/min/µg; the GUS activity in the cotyledon of a soybean line #35 that was controlled by the promoter pRPS28 was 38 pmolMU/min/µg; the GUS activity in the cotyledon of a soybean line #13 that was controlled by the promoter pEIF1-I was 42.77 pmolMU/min/µg; the GUS activity in the cotyledon of a soybean line #77 that was controlled by the promoter pEIF1 was 26.92 pmolMU/min/µg. From the results, the promoters pRPS28-I, pEIF1 and pEIF1-I promoted high levels of expression of a foreign protein in specific tissues of soybean and hence were suitable for use in genetic transformation.

Example 4

Transformation of Vectors Comprising GUS Gene into *Arabidopsis thaliana* and Tobacco.

1. Construction of Vectors pRPS28-GUS, pRPS28-I-GUS, pEIF1-GUS and pEIF1-I-GUS in *Arabidopsis thaliana* and Tobacco.

In Example 2, the DNA fragments pRPS28, pRPS28-I, pEIF1 and pEIF1-I were inserted into the vector pCAMBIA1391Z-GUS-HYG (with hygromycin resistance gene) by the seamless cloning method, and the vector pRPS28-GUS-HYG, pRPS28-I-GUS-HYG, pEIF1-GUS-HYG and pEIF1-I-GUS-HYG were constructed and transformed into *Arabidopsis thaliana* and tobacco. PCR amplification was performed as follows:

A 50 µL PCR reaction mixture contained 1 µL of template DNA, 5 µL of 2×Taq Mix, 0.5 µL of primers (i.e. 0.25 µL of BAR-F and 0.25 µL of BAR-R), and ddH2O (deionized water) added to reach a total volume of 50 µL.

The PCR cycling and running parameters were described as follows: denaturation at 94° C. for 2 min; 30 cycles of 94° C. for 10 s, 58° C. for 30 s, 72° C. for 30 s; and the final extension at 72° C. for 5 min.

The recombinant vector pRPS28-GUS-HYG was amplified using the following primers:
pRPS28-GUS-HYG-F:

```
pRPS28-GUS-HYG-F:
                                          (SEQ ID NO: 14)
GACCATGATTACGCCAAGCTTCACCACCCAATCCATAACCACCAC pRPS28-GUS-HYG-R:
                                          (SEQ ID NO: 13)
CCAGTGAATTCCCGGGGATCCCTGATGCAAAACACGAACAAAGAAAG
```

The recombinant vector pRPS28-I-GUS-HYG was amplified using the following primers:

```
pRPS28-I-GUS-HYG-F:
                                          (SEQ ID NO: 14)
GACCATGATTACGCCAAGCTTCACCACCCAATCCATAACCACCAC
```

-continued pRPS28-I-GUS-HYG-R:
(SEQ ID NO: 15)
CCAGTGAATTCCCGGGGATCC CCTGCTCAAACACAATCAACAG The recombinant vector pEIF1-GUS-HYG was amplified using the following primers:

pEIF1-GUS-HYG-F:
(SEQ ID NO: 16)
GACCATGATTACGCCAAGCTT GGAGAGAAGTTGAACTCTGAGTTGTG pEIF1-GUS-HYG-R:
(SEQ ID NO: 24)
CCAGTGAATTCCCGGGGATCC CTGATCGTAAATTTAAGGTTTCG

The recombinant vector pEIF1-I-GUS-HYG was amplified using the following primers:

pEIF1-I-GUS-HYG-F:
(SEQ ID NO: 16)
GACCATGATTACGCCAAGCTT GGAGAGAAGTTGAACTCTGAGTIGTG pEIF-I-GUS-HYG-R:
(SEQ ID NO: 17)
CCAGTGAATTCCCGGGGATCC AAAACTTGACTCACTAAGACCAAAGG

2. Analysis of GUS Expression Driven by Promoters pRPS28 and pEIF1 in *Arabidopsis thaliana*.

The *Agrobacterium* strain GV3101 comprising pRPS28-GUS-HYG, pRPS28-I-GUS-HYG, pEIF1-GUS-HYG, pEIF1-I-GUS-HYG recombinant vectors were resuspended in a buffer, transformed into *Arabidopsis thaliana* Col-0 by inflorescence dip method, and screened to obtain the transgenic *Arabidopsis thaliana* plants. The GUS protein was expressed in the same level in the transgenic lines #5, #25 and #38 comprising the recombinant vector pRPS28-GUS-HYG; the GUS protein was expressed in the same level in the transgenic lines #2, #5 and #13 transfected with the recombinant vector pRPS28-I-GUS-HYG; the GUS protein was expressed in the same level in the transgenic lines #3, #7 and #12 transfected with the recombinant vector pEIF1-GUS-HYG; the GUS protein was expressed in the same level in the transgenic lines #10, #11 and #12 transfected with the recombinant vector pEIF1-I-GUS-HYG; the seedlings of the T3 transgenic lines were planted in a coculture medium comprising hygromycin and then vernalized in a 4° C. refrigerator for 2 days.

3) The seedlings were transferred in the incubator (at 22±2° C. with 16 hour of light and 8 hour of darkness) for 7 days; and GUS staining was performed on five positive seedlings of T3 generation of each line. The five positive seedlings of T3 generation of each line were planted in the same pod and grown at 22±2° C. with 16 hour of light and 8 hour of darkness. The flower and pod of *Arabidopsis thaliana* were stained for GUS activity.

FIGS. 8A-8D showed the relative expression of GUS protein under control of the promoters pRPS28, pRPS28-I and pGmUbi in different tissues of the T3 transgenic soybean plants. FIG. 8A showed the fluorescence results of GUS protein expression driven by the promoter pRPS28 in the whole plant, flower and pod of *Arabidopsis thaliana*; and FIG. 8B showed the fluorescence results of GUS protein expression driven by the promoter pRPS28-1 in the whole plant, flower and pod of *Arabidopsis thaliana*. The results showed that the promoter pRPS28 promoted the heterologous expression of the target gene (GUS gene) in *Arabidopsis thaliana*.

Figure 9A:
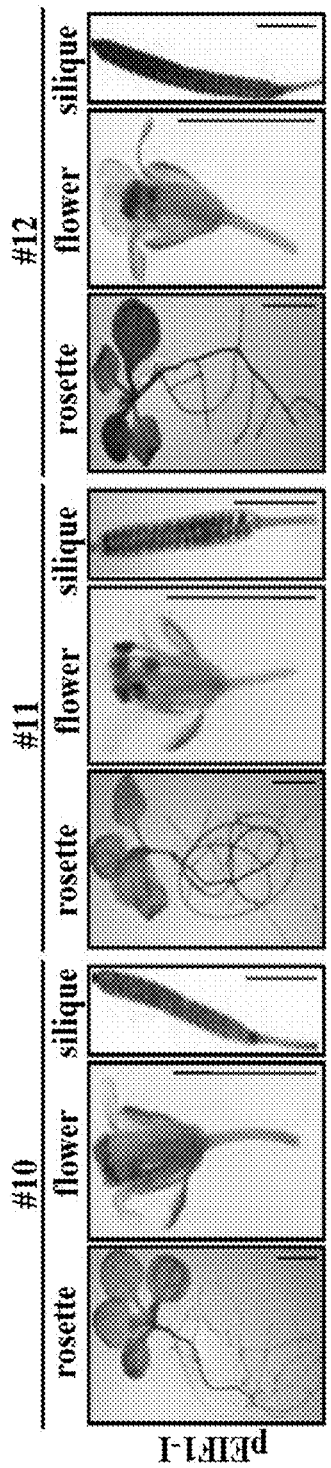
FIGS. 9A-9B show the relative expression of GUS protein under control of the promoters pEIF1 and pEIF1-I in T3 transgenic soybean plants.
Figure 9B:
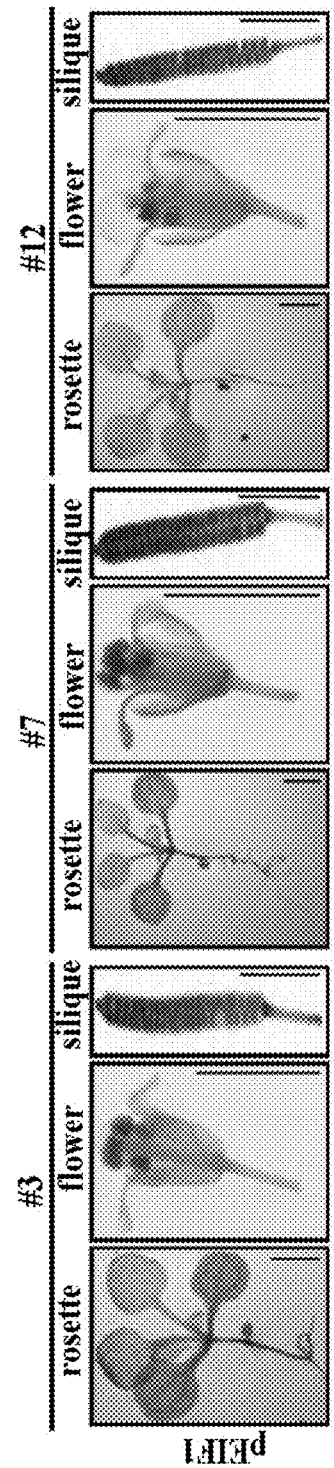

FIGS. 9A-9B showed the relative expression of GUS protein under control of the promoters pEIF1 and pEIF1-I in different tissues of the T3 transgenic soybean plants; where FIG. 9A showed the fluorescence results of GUS protein expression driven by the promoter pEIF1 in the whole plant, flower and pod of *Arabidopsis thaliana*; and FIG. 9B showed the fluorescence results of GUS protein expression driven by the promoter pEIF1-I in the whole plant, flower and pod of *Arabidopsis thaliana*. The results showed that the promoter pEIF1 promoted the heterologous expression of the target gene (GUS gene) in *Arabidopsis thaliana*.

3. Analysis of GUS Expression Driven by Promoters pRPS28 and PEIF1 in Tobacco Leaves.

The *Agrobacterium* strain GV3101 comprising the recombinant vectors pRPS28-GUS-HYG, pRPS28-I-GUS-HYG, pEIF1-GUS-HYG and pEIF1-I-GUS-HYG were resuspended in an infiltration solution; the infiltration solution was injected via a syringe into the leaves of *N. benthamiana* plants; the leaves were subsequently co-cultivated for 2 days and immersed in a GUS staining solution.

Figure 10:
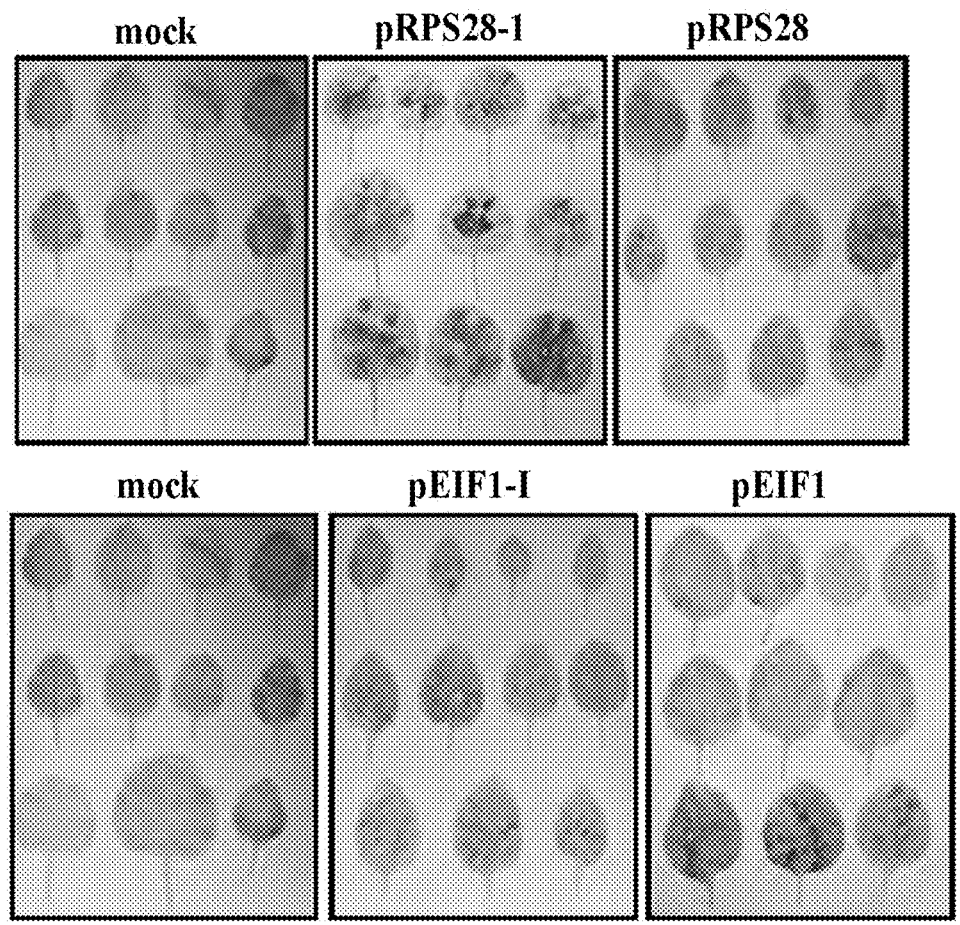
FIG. 10 shows the transient expression of GUS protein under control of the promoters pRPS28 and pRPS28-I in transgenic tobacco leaves.

FIG. 10 showed the transient expression of GUS protein under the control of the promoters pRPS28 and pEIF1 in transgenic tobacco leaves; in the mock, no GUS activity was detected in the tobacco leaves transfected with an empty vector pCAMBIA1391Z; and GUS expression was observed in the leaves transfected with the vector comprising the promoters pRPS28 and pEIF1. From the results, the promoters pRPS28 and pEIF1 promoted the transient and heterologous expression of GUS (target) protein in the tobacco leaves.

What is claimed is:

1. A method for promoting expression of a foreign gene in a plant, the method comprising: constructing a recombinant vector comprising a foreign gene operably linked to a soybean gene promoter pRPS28 or an intron-comprising soybean gene promoter pRPS28-I, and introducing the recombinant vector into the plant; the promoter pRPS28 being represented by SEQ ID NO: 2, and the intron-comprising promoter pRPS28-I being represented by SEQ ID NO: 3.

2. The method of claim 1, wherein the foreign gene is a beta-glucuronidase (GUS) gene.

3. The method of claim 1, wherein the plant is soybean, and the expression of the foreign gene occurs in cotyledons, radicles, plumules, true leaves, compound leaves, buds, petioles, internodes, roots and root nodules of the soybean.

4. The method of claim 1, wherein the plant is *Arabidopsis*, and the expression of the foreign gene occurs in whole plant, flower and pod of the *Arabidopsis*.

5. The method of claim 1, wherein the plant is tobacco, and the expression of the foreign gene occurs in leaves of the tobacco.

6. A method for preparing a recombinant vector comprising a soybean gene promoter, the method comprising inserting a soybean gene promoter pRPS28 or pRPS28-I into a vector pCAMBIA1391Z-BAR, wherein inserting the soybean gene promoter pRPS28 or pRPS28-I into the vector pCAMBIA1391Z-BAR comprises using a PCR amplification fragment of pRPS28 or pRPS28-I as a template, and cloning the PCR amplification fragment into a soybean stable transformation vector pCAMBIA1391Z-BAR by a seamless cloning method to obtain a soybean stable transformation vector pRPS28-GUS-BAR or pRPS28-I-GUS-BAR; wherein:

the vector pCAMBIA1391Z-BAR is obtained by linearizing a vector pCAMBIA1391Z with a restriction enzyme XhoI, and replacing a gene HygR with a gene BAR by the seamless cloning method;

the recombinant vector pRPS28-GUS-BAR is amplified using the following primers:

pRPS28-GUS-BAR-F:
(SEQ ID NO: 14)
GACCATGATTACGCCAAGCTTCACCACCCAATCCATAACCACCAC;

pRPS28-GUS-BAR-R:
(SEQ ID NO: 13)
CCAGTGAATTCCCGGGGATCCCTGATGCAAAACACGAACAAAGAAAG;

the recombinant vector pRPS28-I-GUS-BAR is amplified using the following primers:

pRPS28-I-GUS-BAR-F:
(SEQ ID NO: 14)
GACCATGATTACGCCAAGCTTCACCACCCAATCCATAACCACCAC;

pRPS28-I-GUS-BAR-R:
(SEQ ID NO: 15)
CCAGTGAATTCCCGGGGATCC CCTGCTCAAACACAATCAACAG; and the promoter pRPS28 has the nucleotide sequence of SEQ ID NO: 2, and the promoter pRPS28-I has the nucleotide sequence of SEQ ID NO: 3.

* * * * *

SEQUENCE LISTING

```
Sequence total quantity: 30
SEQ ID NO: 1           moltype = DNA  length = 538
FEATURE                Location/Qualifiers
source                 1..538
                       mol_type = other DNA
                       organism = synthetic construct
SEQUENCE: 1
aattttctc tctcgtctcg tggaagtgta agcaagcaaa accctagcgg cgcctgcttt    60
ctttgttcgt gttttgcatc agatggagtc tcaggtgaag cacgcacttg ttgtcaaagt   120
tatgggtcgt actggatcca gaggacaagt gacccaggtt agagtgaagt ttttggatga   180
tcagaaccgt cacatcatga ggaatgtgaa aggacctgtg agagaaggag acattctcac   240
cctactcgag tctgaaaggg aagcaagaag attgcgctag atggtctctt tttttttggct  300
tgcctccaaa ttcgaacaaa agcaatattt ttcttgatat ttatggtagt tagtcggtgc   360
taaaggggtt atagcaccct atcttattgt tttggatcta ttttcattcg aattattgct   420
tgaattttgt atgtttaaac ttcgagattg aggtatgctt tggtttaata tatgatttga   480
attatggctt aaatttgga ttaatatatg atatgtcttc tatatatggc gccattcc     538
```

```
SEQ ID NO: 2            moltype = DNA   length = 1582
FEATURE                 Location/Qualifiers
source                  1..1582
                        mol_type = other DNA
                        organism = synthetic construct
SEQUENCE: 2
caccacccaa tccataacca ccacaccatc tccatcctat atctgaacat agcgacccca    60
atgctggccg cgtgcagcac cagcacggtc caacaacgtc gcgccactct gatgcaatcc   120
tccctaggaa gggaccaatc actagaacca tgagcaagag gctccaagaa gattgggcta   180
gagctgctga agaaggccct agggttctca tgaaccttag ggtagatttc tgagcccatg   240
ggccaaggtt gggtccaatt atctttgtac atattagact aggatgtcat tatatttggt   300
ccttgtatat agggctccat attgtaggta gggtacccta gaaatatagg attttttcagc  360
ccttgtatttt ttgggcacct agactagttt ttgtattagg ggtagttttg taatttcaca   420
tgcactaagt ggatatttga tgtgtgtggt tggaaataaa tttaattgaa ttggtagaag   480
cccaatccaa ttaaatttta gaggggggagg tgagcatttg cttactacac cccattgcca   540
catcatatag tcacactttg tgcatgtcct tcatgctttt catgcctcat gacacctaag   600
cacacttagt ggagaatctt gtaattgatc ttggattagt gggctgaacc ataactaaaa   660
ttcactaatc ataattagtg aaattttggc tccaaagttt ggctccacaa attcaatttc   720
aaattcaagt gaaatttgaa tttccctcca attttgtgtg acacttaggt tataaataga   780
ggtcatgtgt gtgtattttt ttcaactttg atcatttgaa tattaaactt cagatttcaa   840
agctcattta gagcacaaaa tttcgtgctc ttctctccct ctcccttcat tcatctcctt   900
cttcctccaa gctcttatcc atggcctcct atggtggtga gcttcttcta gactcatctt   960
ctccttgaag tggcgtctcc tctctctctc cctttctcca ttccgctgcc gttcatcttc  1020
caagaagcaa aggaatccat tgatgaagaa gatcctaggc ctacaagctc caatggagct  1080
tgcatcacac tccctaccca cgacccacga ccccctacgcg cacgacctca atctctgagg  1140
ctcttcgtgt gtgactctct atcttcagat atgggttctt gggtttggg attttttggat  1200
ttgtttgggtt tctaggtttg ggatggagac cggggtctat ggtgtcgggg tggttgttgt  1260
tccaatgatg ttaagccaac aatggaaaca cgatttcatt tttggaatta cataaaaact  1320
caaccacgtg gatagtgaca ataatacttt tggtggtgcc aatagtagct tcccaagact  1380
tatttatttt tatgtgttat tttttttttgg ccttggcccg ttgattagaa aaaaataata  1440
cgaaggttaa aaacgtcatt tttgaattat taggccctat ataaatttcg ggaggggcta  1500
aattttttctc tctcgtctcg tggaagtgta agcaagcaaa accctagcgg cgcctgcttt  1560
ctttgttcgt gttttgcatc ag                                           1582

SEQ ID NO: 3            moltype = DNA   length = 2357
FEATURE                 Location/Qualifiers
source                  1..2357
                        mol_type = other DNA
                        organism = synthetic construct
SEQUENCE: 3
caccacccaa tccataacca ccacaccatc tccatcctat atctgaacat agcgacccca    60
atgctggccg cgtgcagcac cagcacggtc caacaacgtc gcgccactct gatgcaatcc   120
tccctaggaa gggaccaatc actagaacca tgagcaagag gctccaagaa gattgggcta   180
gagctgctga agaaggccct agggttctca tgaaccttag ggtagatttc tgagcccatg   240
ggccaaggtt gggtccaatt atctttgtac atattagact aggatgtcat tatatttggt   300
ccttgtatat agggctccat attgtaggta gggtacccta gaaatatagg attttttcagc  360
ccttgtatttt ttgggcacct agactagttt ttgtattagg ggtagttttg taatttcaca   420
tgcactaagt ggatatttga tgtgtgtggt tggaaataaa tttaattgaa ttggtagaag   480
cccaatccaa ttaaatttta gaggggggagg tgagcatttg cttactacac cccattgcca   540
catcatatag tcacactttg tgcatgtcct tcatgctttt catgcctcat gacacctaag   600
cacacttagt ggagaatctt gtaattgatc ttggattagt gggctgaacc ataactaaaa   660
ttcactaatc ataattagtg aaattttggc tccaaagttt ggctccacaa attcaatttc   720
aaattcaagt gaaatttgaa tttccctcca attttgtgtg acacttaggt tataaataga   780
ggtcatgtgt gtgtattttt ttcaactttg atcatttgaa tattaaactt cagatttcaa   840
agctcattta gagcacaaaa tttcgtgctc ttctctccct ctcccttcat tcatctcctt   900
cttcctccaa gctcttatcc atggcctcct atggtggtga gcttcttcta gactcatctt   960
ctccttgaag tggcgtctcc tctctctctc cctttctcca ttccgctgcc gttcatcttc  1020
caagaagcaa aggaatccat tgatgaagaa gatcctaggc ctacaagctc caatggagct  1080
tgcatcacac tccctaccca cgacccacga ccccctacgcg cacgacctca atctctgagg  1140
ctcttcgtgt gtgactctct atcttcagat atgggttctt gggtttgggg attttttggat  1200
ttgtttgggtt tctaggtttg ggatggagac cggggtctat ggtgtcgggg tggttgttgt  1260
tccaatgatg ttaagccaac aatggaaaca cgatttcatt tttggaatta cataaaaact  1320
caaccacgtg gatagtgaca ataatacttt tggtggtgcc aatagtagct tcccaagact  1380
tatttatttt tatgtgttat tttttttttgg ccttggcccg ttgattagaa aaaaataata  1440
cgaaggttaa aaacgtcatt tttgaattat taggccctat ataaatttcg ggaggggcta  1500
aattttttctc tctcgtctcg tggaagtgta agcaagcaaa accctagcgg cgcctgcttt  1560
ctttgttcgt gttttgcatc aggtgcgaac tcacctatt gatttctatc acagctgat   1620
cctcttctc taattaattt attattattt ttcatgtatt gttctcgctt cactgcttct  1680
tatttggctc cgtcatttga aattgttttc ttttaattca agtttcaaat tttcaatatc  1740
tgttactgtg tttatgattt caattttcatg gtgagattat tattgctttc tacgtgacgt  1800
tgaatttgta ctgtatgtgt tgatcttttg ttcttaattt gggtcgcata gtgtttgtgg  1860
cttgtttggt gaagtaacgt agaccccgagt gttctaacaa atgatatgtt ggattctttc  1920
attagcatgc ttttttggaat ttttgacctt tggaagtcgt atactgttca gcatcactaa  1980
atttagtcct ccctcaacaa aagaatctgg tgtaggatgc aatcatcaa atgaaacaag   2040
gtttatgctg aagtacaaga agactgatct gttattttga tgttattgct ggacttggtt  2100
ttcttttttc cttttatgtg atgtgtgcca tgtccatatt tgtattttta ccctatcagt  2160
tgtttggttc gtgtgaaact gtgaatgctt tgttatttc ctgttacttt ggatgtcttc   2220
aatttaaggt ttttagtctt ctggatttcg aaggtgatac atatttaccct gtcacggtga  2280
ccaattagct gtgatgcatt aaacccaatt gttttccaca ttcatctcat aaaaactgtt  2340
```

```
gattgtgttt gagcagg                                                     2357

SEQ ID NO: 4           moltype = DNA   length = 834
FEATURE                Location/Qualifiers
source                 1..834
                       mol_type = other DNA
                       organism = synthetic construct
SEQUENCE: 4
cttgcgatat cttcactatt aaatatctgt tcttccaacc ataaccacac cacaccgagt        60
cgcagaaaaa gaaaaaagcg atcatagttt cacttcggcc ttatccagtt tagggtttcg       120
gttctctacc ctatctttca cgtatcgaaa ccttaaattt acgatcaggt ctgagcaatc       180
tggttggtag aacctttggt cttagtgagt caagttttat gtctgaatta gacgatcaaa       240
ttcctactgc cttcgatcct tttgctgatg caaatgctga tgactcgggt gctgggtcaa       300
aggagtatgt gcatattcgt gtacagcagc gaaatgctag gaaaagcctg acaaccgttc       360
agggattgaa aaaggaattc agctataaca agatacttaa agacgtcaag aaagagttcc       420
gttgcaatgg aacagttgtt caggacccag aactaggaca ggttattcaa cttcaaggtg       480
atcagaggaa gaatgtttct accttcctag tccaggctgg tatcgtgaag aaggatcata       540
tcaagattca tggtttctga gcggttggag tcttaagtgt caaattttac ctgcctgact       600
atgtgttagg cataatatat aatctgagtc gtgtggatgt gattgtggta tttctaatgt       660
gttcttatgt tttaccatgt gatgtgggat tatggatttc agaacattgt gtgttatttg       720
cttttgaagac ttatatgaaa acggtttaat ggaccccgt atttaatctt atttcattta       780
gaacatataa aaaatgtagc tttgaaggct cgagctcttg taagctgtcg cttc            834

SEQ ID NO: 5           moltype = DNA   length = 1640
FEATURE                Location/Qualifiers
source                 1..1640
                       mol_type = other DNA
                       organism = synthetic construct
SEQUENCE: 5
ggagagaagt tgaactctga gttgtgtctc acaagactct cattcatcaa agttacaaca        60
agtgttacac atgcttctat ttatagacta ggtagcttcc ttgagaagct ttcttgagaa       120
aactttcttg agaagcttct ttgagaaaac ttccttgaga agctagagct tagctacaca       180
cacccctcta ataactaagc tcacctcctt gagaagcttc cttgagaaga ttcctaaaaa       240
agctagagct tagttacaca caccccctat aatagctaag ctcaccccca tgccaaaata       300
catgaaaata taaaaaaaaa tctctattac aaagattact caaaatgccc tgaaatacaa       360
ggctaaaacc ctatactact agaatggcca aaatacaagg ctcaaaagaa ggaaaaccca       420
attctaacat ttacaaagaa gaatggatcc aaccttgacc catgggctca aaaatctacc       480
ctaaggttca tgagaacctt agggccttct ttagtagctc tagcccaagc ctcttggagt       540
cttctatcca atacccttgg ggggtaggat tacatcagac tagacaattc aaaaaatatt       600
tgtccaacat ttgatttaaa aaatgactga gggataggac aaaataaaga aggatggact       660
ggatgaatac ccaaaaactt gtaactcact aaacttccat acaactttt gtctagtgtc        720
taacaaaagt aaaaatacaa tactattcct attttttgact tttcattatt tcacaccttc       780
tttcttattc catatgcgcc tcattctcca aatattaaca agctcatcgc cctcctatcc       840
atcatcgtgc tggagctctc ccaattcgcc tccaccatac cccttatcgt ggatctctca       900
gaccactcct ccctctccat tctcttcgtc cccaacacct acctgctgc cgacgaccac       960
cacttctccc cgaccacctt catcgacgcc aatcgctacc acttcctcct ccaattcctt      1020
tcttgtccg acctttcgt cttcccccctt ggcaagctca tcaccacact tcttcaaatc      1080
accgccgtg ctaccaacaa tttcagtttc gtgaacctca tctgcgactc tcattctaat      1140
gtcatctcaa tccggtttcc cgcgactctt aatctaatgt tttccattaa tggacattag      1200
ctaatatttt taatggaaaa cataaaaaat gactaaaaga aaactcttaa tataactat       1260
taaaatatat atttttaaa tttataaaat gacagtgaaa tataataaat caatagtaat      1320
atttaattta ataaaaatat ttaaacataa atcttattat tttaaaatta attttacaaa      1380
attaattat ttaaaatcaa ttttatgaat gctgatataa gtatcgactt tattccctgt      1440
ttttcggatc ataacgtg acacgcgtgc ttccttgcgat atcttcacta ttaaaatatct      1500
gttcttccaa ccataaccac accacaccga gtcgcagaaa agaaaaaaag cgatcatagt      1560
ttcacttcgg ccttatccag tttagggttt cggttctcta ccctatcttt cacgtatcga      1620
aaccttaaat ttacgatcag                                                 1640

SEQ ID NO: 6           moltype = DNA   length = 2370
FEATURE                Location/Qualifiers
source                 1..2370
                       mol_type = other DNA
                       organism = synthetic construct
SEQUENCE: 6
ggagagaagt tgaactctga gttgtgtctc acaagactct cattcatcaa agttacaaca        60
agtgttacac atgcttctat ttatagacta ggtagcttcc ttgagaagct ttcttgagaa       120
aactttcttg agaagcttct ttgagaaaac ttccttgaga agctagagct tagctacaca       180
cacccctcta ataactaagc tcacctcctt gagaagcttc cttgagaaga ttcctaaaaa       240
agctagagct tagttacaca caccccctat aatagctaag ctcaccccca tgccaaaata       300
catgaaaata taaaaaaaaa tctctattac aaagattact caaaatgccc tgaaatacaa       360
ggctaaaacc ctatactact agaatggcca aaatacaagg ctcaaaagaa ggaaaaccca       420
attctaacat ttacaaagaa gaatggatcc aaccttgacc catgggctca aaaatctacc       480
ctaaggttca tgagaacctt agggccttct ttagtagctc tagcccaagc ctcttggagt       540
cttctatcca atacccttgg ggggtaggat tacatcagac tagacaattc aaaaaatatt       600
tgtccaacat ttgatttaaa aaatgactga gggataggac aaaataaaga aggatggact       660
ggatgaatac ccaaaaactt gtaactcact aaacttccat acaactttt gtctagtgtc        720
taacaaaagt aaaaatacaa tactattcct attttttgact tttcattatt tcacaccttc       780
tttcttattc catatgcgcc tcattctcca aatattaaca agctcatcgc cctcctatcc       840
atcatcgtgc tggagctctc ccaattcgcc tccaccatac cccttatcgt ggatctctca       900
```

```
gaccactcct ccctctccat tctcttcgtc cccaacacct acctcgctgc cgacgaccac   960
cacttctccc cgaccacctt catcgacgcc aatcgctacc acttcctcct ccaattcctt  1020
tcttggtccg acctttgcgt cttccccctt ggcaagctca tcaccacact tcttcaaatc  1080
accgcccgtg ctaccaacaa tttcagtttc gtgaacctca tctgcgactc tcattctaat  1140
gtcatctcaa tccggtttcc cgcgactctt aatctaatgt tttccattaa tggacattag  1200
ctaatatttt taatggaaaa cataaaaaat gactaaaaga aaactcttaa tataacttat  1260
taaaatatat attttttaaa tttataaaat gacagtgaaa tataataaat caatagtaat  1320
atttaattta ataaaaatat ttaaacataa atcttattat tttaaaatta attttacaaa  1380
attaatttat ttaaaatcaa ttttatgaat gctgatataa gtatcgactt tattccctgt  1440
ttttcggatc ataacacgtg acacgcgtgc ttccttgcgat atcttcacta ttaaatatct  1500
gttcttccaa ccataaccac accacaccga gtcgcagaaa aagaaaaaag cgatcatagt  1560
ttcacttcgg ccttatccag tttagggttt cggttctcta ccctatcttt cacgtatcga  1620
aaccttaaat ttacgatcag gtaatctccg atcattttt ctcagatttg atttatcttc  1680
cgcgctaatt ttagggttcg actttcgctt tgtctcccat gatctaagtt tgactcaatt  1740
ttcttttctg ctttttttcc ccgttaccgt acatttttt tggggttcga tatatttttt  1800
atcagatctt tcagctataa atcgtgtatt tgttgttagt gaaaagtgtt ttttttttcc  1860
ttttcctaat tcagtatttc attttgattt aagtgtacga tgattttga gttatgggct  1920
tttttttttct gtgataactt tttgacggtg tggttgctag attgtcacca tgaactatat  1980
caattttaag tcaaaacctg taatctagga aagcattctg ttttatgctg ctgagatctt  2040
ttgaatgtat ctaaagttga aactaattgt gggatttttt taatcgcttt cattttaaat  2100
cattcagttg cattatttt ggtgttttta atttgaagca aagtaatta ggtaggcaat    2160
tttaataca tgggatggtc attgctgata tcttccttcg ttgggtgtg tgaagattgt    2220
tttgatgcga tgattaatga cactggtttt gcttttgaat ttttgtaaag tttgctatta  2280
tagtaattca atttaactaa catgttgatt ttattttcag gtctgagcaa tctggttggt  2340
agaacctttg gtcttagtga gtcaagtttt                                   2370

SEQ ID NO: 7            moltype = DNA   length = 552
FEATURE                 Location/Qualifiers
source                  1..552
                        mol_type = other DNA
                        organism = synthetic construct
SEQUENCE: 7
atgagcccag aacgacgccc ggccgacatc cgccgtgcca ccgaggcgga catgccggcg     60
gtctgcacca tcgtcaacca ctacatcgag acaagcacgg tcaacttccg taccgagccg    120
caggaaccgc aggagtggac ggacgacctc gtccgtctgc gggagcgcta tccctggctc    180
gtcgccgagg tggacggcga ggtcgccggc atcgcctacg cgggccccctg gaaggcacgc    240
aacgcctacg actggacggc cgagtcgacc gtgtacgtct cccccccgcca ccagcggacg    300
ggactgggct ccacgctcta cacccacctg ctgaagtccc tggaggcaca gggcttcaag    360
agcgtgctcg ctgtcatcgg gctgcccaac gacccgacgc tgatgcatgc ca cgaggcgctc 420
ggatatgccc ccgcggcat gctgcgggcg gccggcttca agcacgggaa ctggcatgac    480
gtgggtttct ggcagctgga cttcagcctg ccggtaccgc ccgtccggt cctgcccgtc    540
accgagatct ga                                                      552

SEQ ID NO: 8            moltype = DNA   length = 21
FEATURE                 Location/Qualifiers
source                  1..21
                        mol_type = other DNA
                        organism = synthetic construct
SEQUENCE: 8
atggagtctc aggtgaagca c                                              21

SEQ ID NO: 9            moltype = DNA   length = 21
FEATURE                 Location/Qualifiers
source                  1..21
                        mol_type = other DNA
                        organism = synthetic construct
SEQUENCE: 9
ctagcgcaat cttcttgctt c                                              21

SEQ ID NO: 10           moltype = DNA   length = 26
FEATURE                 Location/Qualifiers
source                  1..26
                        mol_type = other DNA
                        organism = synthetic construct
SEQUENCE: 10
atgtctgaat tagacgatca aattcc                                         26

SEQ ID NO: 11           moltype = DNA   length = 27
FEATURE                 Location/Qualifiers
source                  1..27
                        mol_type = other DNA
                        organism = synthetic construct
SEQUENCE: 11
tcagaaacca tgaatcttga tatgatc                                        27

SEQ ID NO: 12           moltype = DNA   length = 44
FEATURE                 Location/Qualifiers
source                  1..44
                        mol_type = other DNA
```

```
                              organism = synthetic construct
SEQUENCE: 12
gaccatgatt acgccaagct tcaccaccca atccataacc acca                    44

SEQ ID NO: 13         moltype = DNA  length = 47
FEATURE               Location/Qualifiers
source                1..47
                      mol_type = other DNA
                      organism = synthetic construct
SEQUENCE: 13
ccagtgaatt cccggggatc cctgatgcaa aacacgaaca aagaaag                 47

SEQ ID NO: 14         moltype = DNA  length = 45
FEATURE               Location/Qualifiers
source                1..45
                      mol_type = other DNA
                      organism = synthetic construct
SEQUENCE: 14
gaccatgatt acgccaagct tcaccaccca atccataacc accac                   45

SEQ ID NO: 15         moltype = DNA  length = 43
FEATURE               Location/Qualifiers
source                1..43
                      mol_type = other DNA
                      organism = synthetic construct
SEQUENCE: 15
ccagtgaatt cccggggatc ccctgctcaa acacaatcaa cag                     43

SEQ ID NO: 16         moltype = DNA  length = 47
FEATURE               Location/Qualifiers
source                1..47
                      mol_type = other DNA
                      organism = synthetic construct
SEQUENCE: 16
gaccatgatt acgccaagct tggagagaag ttgaactctg agttgtg                 47

SEQ ID NO: 17         moltype = DNA  length = 47
FEATURE               Location/Qualifiers
source                1..47
                      mol_type = other DNA
                      organism = synthetic construct
SEQUENCE: 17
ccagtgaatt cccggggatc caaaacttga ctcactaaga ccaaagg                 47

SEQ ID NO: 18         moltype = DNA  length = 41
FEATURE               Location/Qualifiers
source                1..41
                      mol_type = other DNA
                      organism = synthetic construct
SEQUENCE: 18
gaccatgatt acgccaagct tgggcccaat ataacaacga c                       41

SEQ ID NO: 19         moltype = DNA  length = 41
FEATURE               Location/Qualifiers
source                1..41
                      mol_type = other DNA
                      organism = synthetic construct
SEQUENCE: 19
ccagtgaatt cccggggatc cctgtcgagt caacaatcac a                       41

SEQ ID NO: 20         moltype = DNA  length = 42
FEATURE               Location/Qualifiers
source                1..42
                      mol_type = other DNA
                      organism = synthetic construct
SEQUENCE: 20
tacaaatcta tctctctcga gatgagccca gaacgacgcc cg                      42

SEQ ID NO: 21         moltype = DNA  length = 46
FEATURE               Location/Qualifiers
source                1..46
                      mol_type = other DNA
                      organism = synthetic construct
SEQUENCE: 21
cattattatg gagaaactcg agtcagatct cggtgacggg caggac                  46

SEQ ID NO: 22         moltype = DNA  length = 24
FEATURE               Location/Qualifiers
source                1..24
```

```
                        mol_type = other DNA
                        organism = synthetic construct
SEQUENCE: 22
atgagcccag aacgacgccc ggcc                                              24

SEQ ID NO: 23           moltype = DNA  length = 24
FEATURE                 Location/Qualifiers
source                  1..24
                        mol_type = other DNA
                        organism = synthetic construct
SEQUENCE: 23
ttagatctcg gtgacgggca ggac                                              24

SEQ ID NO: 24           moltype = DNA  length = 44
FEATURE                 Location/Qualifiers
source                  1..44
                        mol_type = other DNA
                        organism = synthetic construct
SEQUENCE: 24
ccagtgaatt cccggggatc cctgatcgta aatttaaggt ttcg                        44

SEQ ID NO: 25           moltype = DNA  length = 24
FEATURE                 Location/Qualifiers
source                  1..24
                        mol_type = other DNA
                        organism = synthetic construct
SEQUENCE: 25
caccacccaa tccataacca ccac                                              24

SEQ ID NO: 26           moltype = DNA  length = 26
FEATURE                 Location/Qualifiers
source                  1..26
                        mol_type = other DNA
                        organism = synthetic construct
SEQUENCE: 26
ctgatgcaaa acacgaacaa agaaag                                            26

SEQ ID NO: 27           moltype = DNA  length = 22
FEATURE                 Location/Qualifiers
source                  1..22
                        mol_type = other DNA
                        organism = synthetic construct
SEQUENCE: 27
cctgctcaaa cacaatcaac ag                                                22

SEQ ID NO: 28           moltype = DNA  length = 26
FEATURE                 Location/Qualifiers
source                  1..26
                        mol_type = other DNA
                        organism = synthetic construct
SEQUENCE: 28
ggagagaagt tgaactctga gttgtg                                            26

SEQ ID NO: 29           moltype = DNA  length = 23
FEATURE                 Location/Qualifiers
source                  1..23
                        mol_type = other DNA
                        organism = synthetic construct
SEQUENCE: 29
ctgatcgtaa atttaaggtt tcg                                               23

SEQ ID NO: 30           moltype = DNA  length = 26
FEATURE                 Location/Qualifiers
source                  1..26
                        mol_type = other DNA
                        organism = synthetic construct
SEQUENCE: 30
aaaacttgac tcactaagac caaagg                                            26
```